(12) United States Patent
Schmura et al.

(10) Patent No.: US 11,291,482 B2
(45) Date of Patent: Apr. 5, 2022

(54) ROD REDUCERS AND RELATED METHODS

(71) Applicant: Medos International Sarl, Le Locle (CH)

(72) Inventors: Kurt Schmura, Middleboro, MA (US); Raymond F. Murphy, Attleboro, MA (US); Frank Spratt, Middleboro, MA (US); Albert Montello, Duxbury, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 176 days.

(21) Appl. No.: 16/360,199

(22) Filed: Mar. 21, 2019

(65) Prior Publication Data

US 2020/0297396 A1 Sep. 24, 2020

(51) Int. Cl.
*A61B 17/70* (2006.01)
*A61F 2/46* (2006.01)

(52) U.S. Cl.
CPC ........ *A61B 17/7086* (2013.01); *A61F 2/4611* (2013.01); *A61B 2560/0425* (2013.01)

(58) Field of Classification Search
CPC ............ A61B 17/7086; A61B 17/7085; A61B 17/7083
See application file for complete search history.

(56) References Cited

U.S. PATENT DOCUMENTS

| | | | |
|---|---|---|---|
| 410,780 A | 9/1889 | Cahn | |
| 1,470,313 A | 10/1923 | Woolen | |
| 1,628,144 A | 5/1927 | Herrmann | |
| 1,709,766 A | 4/1929 | Bolton | |
| 1,889,330 A | 11/1932 | Humes et al. | |
| 1,925,385 A | 9/1933 | Humes et al. | |
| 2,113,246 A | 4/1938 | Frederick | |
| 2,248,054 A | 7/1941 | Becker | |
| 2,248,057 A | 7/1941 | Bond | |
| 2,291,413 A | 7/1942 | Siebrandt | |
| 2,370,407 A | 2/1945 | McCartney | |
| 2,800,820 A | 7/1957 | Retterath | |

(Continued)

FOREIGN PATENT DOCUMENTS

| | | |
|---|---|---|
| CN | 102488548 B | 9/2013 |
| DE | 4238339 A1 | 5/1994 |

(Continued)

OTHER PUBLICATIONS

International Search Report and Written Opinion for PCT/US2018/065497, dated Jul. 8, 2019 (22 pages).

*Primary Examiner* — Julianna N Harvey
(74) *Attorney, Agent, or Firm* — Barnes & Thornburg LLP

(57) ABSTRACT

Kerrison-style rod reducers, inline-style rod reducers, and related methods of using the disclosed rod reducers for holding a spinal implant and seating a fixation rod in a rod-receiving portion of the spinal implant are provided for herein. The disclosed rod reducers can also be configured for applying a set screw or other closure mechanism to secure the rod within the rod-receiving portion of the spinal implant. The disclosed embodiments can be easy to use, not require significant force to operate, and be efficient, thereby reducing the time and expense necessary to perform spinal surgery. The disclosed rod reducers can be readily disassembled, thereby making these surgical instruments easy to clean and sterilize.

17 Claims, 15 Drawing Sheets

(56) References Cited

U.S. PATENT DOCUMENTS

| | | | |
|---|---|---|---|
| 3,960,147 A | 6/1976 | Murray |
| 4,237,875 A | 12/1980 | Termanini |
| 4,271,836 A | 6/1981 | Bacal et al. |
| 4,411,259 A | 10/1983 | Drummond |
| 4,445,513 A | 5/1984 | Ulrich et al. |
| 4,655,223 A | 4/1987 | Kim |
| 4,809,695 A | 3/1989 | Gwathmey et al. |
| 4,896,661 A | 1/1990 | Bogert et al. |
| 5,014,407 A | 5/1991 | Boughten et al. |
| 5,020,519 A | 6/1991 | Hayes et al. |
| D346,217 S | 4/1994 | Sparker et al. |
| 5,306,248 A | 4/1994 | Barrington |
| 5,364,397 A | 11/1994 | Hayes et al. |
| 5,391,170 A | 2/1995 | McGuire et al. |
| 5,429,641 A | 7/1995 | Gotfried et al. |
| 5,431,658 A | 7/1995 | Moskovich |
| 5,484,440 A | 1/1996 | Allard |
| 5,545,165 A | 8/1996 | Biedermann et al. |
| 5,551,320 A | 9/1996 | Horobec et al. |
| 5,616,143 A | 4/1997 | Schlapfer et al. |
| 5,649,931 A | 7/1997 | Bryant et al. |
| 5,672,175 A | 9/1997 | Martin |
| 5,683,399 A | 11/1997 | Jones |
| 5,697,933 A | 12/1997 | Gundlapalli et al. |
| 5,707,371 A | 1/1998 | Metz-Stavenhagen et al. |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,810,878 A | 9/1998 | Burel et al. |
| 5,910,141 A | 6/1999 | Morrison et al. |
| 5,941,885 A | 8/1999 | Jackson |
| 5,951,564 A | 9/1999 | Schroder et al. |
| 5,951,579 A | 9/1999 | Dykes |
| 6,010,509 A | 1/2000 | Delgado et al. |
| 6,036,692 A | 3/2000 | Burel et al. |
| 6,099,528 A | 8/2000 | Saurat et al. |
| 6,123,707 A | 9/2000 | Wagner |
| 6,139,549 A | 10/2000 | Keller |
| 6,183,472 B1 | 2/2001 | Lutz |
| 6,210,330 B1 | 4/2001 | Tepper et al. |
| 6,251,112 B1 | 6/2001 | Jackson |
| 6,258,090 B1 | 7/2001 | Jackson |
| 6,371,973 B1 | 4/2002 | Tepper et al. |
| 6,413,258 B1 | 7/2002 | Bernhardt, Jr. |
| 6,440,133 B1 | 8/2002 | Beale et al. |
| 6,440,142 B1 | 8/2002 | Ralph et al. |
| 6,440,144 B1 | 8/2002 | Bacher |
| 6,511,484 B2 | 1/2003 | Torode et al. |
| 6,530,929 B1 | 3/2003 | Justis et al. |
| 6,554,832 B2 | 4/2003 | Shluzas |
| 6,589,249 B2 | 7/2003 | Sater et al. |
| 6,648,888 B1 | 11/2003 | Shluzas |
| 6,660,006 B2 | 12/2003 | Markworth et al. |
| 6,676,661 B1 | 1/2004 | Martin Benlloch et al. |
| 6,726,692 B2 | 4/2004 | Bette et al. |
| 6,743,231 B1 | 6/2004 | Gray et al. |
| 6,746,449 B2 | 6/2004 | Jones et al. |
| 6,752,832 B2 | 6/2004 | Neumann |
| 6,755,829 B1 | 6/2004 | Bono et al. |
| 6,790,208 B2 | 9/2004 | Oribe et al. |
| 6,790,209 B2 | 9/2004 | Beale et al. |
| 6,827,722 B1 | 12/2004 | Schoenefeld |
| 7,081,117 B2 | 7/2006 | Bono et al. |
| 7,083,621 B2 | 8/2006 | Shaolian et al. |
| 7,090,677 B2 | 8/2006 | Fallin et al. |
| 7,156,849 B2 | 1/2007 | Dunbar et al. |
| 7,179,254 B2 | 2/2007 | Pendekanti et al. |
| 7,179,261 B2 | 2/2007 | Sicvol et al. |
| 7,189,234 B2 | 3/2007 | Zucherman et al. |
| 7,278,995 B2 | 10/2007 | Nichols et al. |
| 7,320,689 B2 | 1/2008 | Keller |
| 7,371,239 B2 | 5/2008 | Dec et al. |
| 7,462,182 B2 | 12/2008 | Lim |
| 7,481,813 B1 | 1/2009 | Purcell |
| 7,485,120 B2 | 2/2009 | Ray |
| 7,491,207 B2 | 2/2009 | Keyer et al. |
| 7,527,638 B2 | 5/2009 | Anderson et al. |
| 7,572,281 B2 | 8/2009 | Runco et al. |
| 7,621,918 B2 | 11/2009 | Jackson |
| 7,651,502 B2 | 1/2010 | Jackson |
| 7,666,188 B2 | 2/2010 | Anderson et al. |
| 7,708,763 B2 | 5/2010 | Selover et al. |
| 7,776,040 B2 | 8/2010 | Markworth et al. |
| 7,806,912 B2 | 10/2010 | Lawton et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,867,237 B2 | 1/2011 | Stad et al. |
| 7,887,539 B2 | 2/2011 | Dunbar, Jr. et al. |
| 7,887,541 B2 | 2/2011 | Runco et al. |
| 7,901,434 B2 | 3/2011 | Drewry et al. |
| 7,922,724 B2 | 4/2011 | Lim |
| 7,931,677 B2 | 4/2011 | Abdelgany |
| 7,988,698 B2 | 8/2011 | Rosenberg et al. |
| 8,109,974 B2 | 2/2012 | Boomer et al. |
| 8,172,847 B2 | 5/2012 | Dziedzic et al. |
| 8,192,438 B2 | 6/2012 | Garamszegi |
| 8,216,241 B2 | 7/2012 | Runco et al. |
| 8,235,997 B2 | 8/2012 | Hoffman et al. |
| 8,246,657 B1 | 8/2012 | Samuel |
| 8,298,269 B2 | 10/2012 | Null et al. |
| 8,303,595 B2 | 11/2012 | Jones |
| 8,308,774 B2 | 11/2012 | Hoffman et al. |
| 8,317,837 B2 | 11/2012 | Rezach et al. |
| 8,337,527 B2 | 12/2012 | Hawkins et al. |
| 8,343,165 B2 | 1/2013 | Berrevoets |
| 8,377,104 B2 | 2/2013 | Jones et al. |
| 8,394,109 B2 | 3/2013 | Hutton et al. |
| 8,430,916 B1 | 4/2013 | Winslow et al. |
| 8,439,922 B1 | 5/2013 | Arnold et al. |
| 8,460,308 B2 | 6/2013 | Marino et al. |
| 8,540,718 B2 | 9/2013 | Dauster et al. |
| 8,556,904 B2 | 10/2013 | Rezach et al. |
| 8,603,145 B2 | 12/2013 | Forton et al. |
| 8,617,165 B2 | 12/2013 | Harper |
| 8,636,742 B2 | 1/2014 | Runco et al. |
| 8,636,776 B2 | 1/2014 | Rosenberg et al. |
| 8,647,347 B2 | 2/2014 | Runco et al. |
| 8,657,857 B2 | 2/2014 | Dall et al. |
| 8,715,323 B2 | 5/2014 | Ballard et al. |
| 8,728,124 B2 | 5/2014 | Miller |
| 8,747,409 B2 | 6/2014 | Ichelmann et al. |
| 8,764,756 B2 | 7/2014 | Jones |
| 8,790,348 B2 | 7/2014 | Stad et al. |
| 8,795,283 B2 | 8/2014 | Petit |
| 8,828,056 B2 | 9/2014 | Buss et al. |
| 8,845,640 B2 | 9/2014 | McLean et al. |
| 8,845,649 B2 | 9/2014 | Jackson |
| 8,870,881 B2 | 10/2014 | Rezach et al. |
| 8,876,869 B1 | 11/2014 | Schafer et al. |
| 8,900,240 B2 | 12/2014 | White et al. |
| 8,906,062 B2 | 12/2014 | Nichols et al. |
| 8,932,296 B2 | 1/2015 | Neary et al. |
| 8,951,289 B2 | 2/2015 | Matityahu |
| 8,956,362 B2 | 2/2015 | Landry et al. |
| 8,979,848 B2 | 3/2015 | Butters et al. |
| 8,986,349 B1 | 3/2015 | German et al. |
| 9,044,272 B2 | 6/2015 | Shaffrey et al. |
| 9,044,274 B2 | 6/2015 | Gunn et al. |
| 9,078,705 B2 | 7/2015 | Matthis et al. |
| 9,078,709 B2 | 7/2015 | McBride |
| 9,084,634 B1 | 7/2015 | Lab et al. |
| 9,119,674 B2 | 9/2015 | Matthis et al. |
| 9,125,694 B2 | 9/2015 | Butler et al. |
| 9,149,307 B2 | 10/2015 | Sandstrom et al. |
| 9,155,567 B2 | 10/2015 | Auerbach et al. |
| 9,186,188 B2 | 11/2015 | Gleason et al. |
| 9,204,901 B2 | 12/2015 | Black et al. |
| 9,204,909 B2 | 12/2015 | Rezach et al. |
| 9,220,543 B2 | 12/2015 | Walker et al. |
| 9,247,969 B2 | 2/2016 | Nunley et al. |
| 9,254,150 B2 | 2/2016 | Biedermann et al. |
| 9,265,533 B2 | 2/2016 | Nelson et al. |

(56) References Cited

U.S. PATENT DOCUMENTS

| | | |
|---|---|---|
| 9,265,538 B2 | 2/2016 | Stad et al. |
| 9,271,768 B2 | 3/2016 | Artaki et al. |
| 9,283,002 B2 | 3/2016 | Larroque-Lahitette et al. |
| 9,308,030 B2 | 4/2016 | Manninen |
| 9,451,994 B1 | 9/2016 | Whipple et al. |
| 9,486,256 B1 | 11/2016 | Lish et al. |
| 9,492,205 B2 | 11/2016 | Alsup et al. |
| 9,498,261 B2 | 11/2016 | McClintock |
| 9,795,417 B2 | 10/2017 | Beger et al. |
| 10,238,432 B2 | 3/2019 | Carruth et al. |
| 10,398,476 B2 | 9/2019 | Lee et al. |
| 10,966,762 B2 | 4/2021 | Lee et al. |
| 2001/0029376 A1 | 10/2001 | Sater et al. |
| 2002/0072752 A1 | 6/2002 | Zucherman et al. |
| 2002/0095153 A1 | 7/2002 | Jones et al. |
| 2003/0009168 A1 | 1/2003 | Beale et al. |
| 2003/0028195 A1 | 2/2003 | Bette |
| 2003/0083747 A1 | 5/2003 | Winterbottom et al. |
| 2003/0125750 A1 | 7/2003 | Zwimmann et al. |
| 2003/0149438 A1 | 8/2003 | Nichols et al. |
| 2003/0171756 A1 | 9/2003 | Fallin et al. |
| 2003/0191370 A1 | 10/2003 | Phillips |
| 2003/0199872 A1 | 10/2003 | Markworth et al. |
| 2003/0225408 A1 | 12/2003 | Nichols et al. |
| 2004/0049191 A1 | 3/2004 | Markworth et al. |
| 2004/0147936 A1 | 7/2004 | Rosenberg et al. |
| 2004/0147937 A1 | 7/2004 | Dunbar et al. |
| 2004/0172057 A1 | 9/2004 | Guillebon et al. |
| 2004/0176779 A1 | 9/2004 | Casutt et al. |
| 2004/0220567 A1 | 11/2004 | Eisermann et al. |
| 2004/0254576 A1 | 12/2004 | Dunbar et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0033299 A1 | 2/2005 | Shluzas |
| 2005/0051648 A1 | 3/2005 | Mercier |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0192570 A1 | 9/2005 | Jackson |
| 2005/0192579 A1 | 9/2005 | Jackson |
| 2005/0228392 A1 | 10/2005 | Keyer et al. |
| 2005/0261702 A1 | 11/2005 | Oribe et al. |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036260 A1 | 2/2006 | Runco et al. |
| 2006/0069391 A1 | 3/2006 | Jackson |
| 2006/0074418 A1 | 4/2006 | Jackson |
| 2006/0079892 A1 | 4/2006 | Roychowdhury et al. |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0166534 A1 | 7/2006 | Brumfield et al. |
| 2006/0166535 A1 | 7/2006 | Brumfield et al. |
| 2006/0229611 A1 | 10/2006 | Avery et al. |
| 2006/0233597 A1 | 10/2006 | Ensign et al. |
| 2006/0293692 A1 | 12/2006 | Whipple et al. |
| 2007/0093849 A1 | 4/2007 | Jones et al. |
| 2007/0100347 A1 | 5/2007 | Stad et al. |
| 2007/0129731 A1 | 6/2007 | Sicvol et al. |
| 2007/0161998 A1 | 7/2007 | Whipple |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0213722 A1 | 9/2007 | Jones et al. |
| 2007/0233097 A1 | 10/2007 | Anderson et al. |
| 2007/0260261 A1 | 11/2007 | Runco et al. |
| 2007/0270817 A1 | 11/2007 | Rezach |
| 2007/0270880 A1 | 11/2007 | Lindemann et al. |
| 2007/0282337 A1 | 12/2007 | Garamszegi |
| 2008/0015601 A1 | 1/2008 | Castro et al. |
| 2008/0058805 A1 | 3/2008 | Stuart |
| 2008/0077134 A1 | 3/2008 | Dziedzic et al. |
| 2008/0077135 A1 | 3/2008 | Stad et al. |
| 2008/0154277 A1 | 6/2008 | Machalk et al. |
| 2008/0195155 A1 | 8/2008 | Hoffman et al. |
| 2008/0228233 A1 | 9/2008 | Hoffman et al. |
| 2008/0243190 A1 | 10/2008 | Dziedzic et al. |
| 2008/0255574 A1 | 10/2008 | Dye |
| 2009/0030419 A1* | 1/2009 | Runco ................ A61B 17/7086 606/99 |
| 2009/0030420 A1 | 1/2009 | Runco et al. |
| 2009/0054902 A1 | 2/2009 | Mickiewicz et al. |
| 2009/0082811 A1 | 3/2009 | Stad et al. |
| 2009/0088764 A1 | 4/2009 | Stad et al. |
| 2009/0105712 A1 | 4/2009 | Dauster et al. |
| 2009/0138056 A1 | 5/2009 | Anderson et al. |
| 2009/0143828 A1 | 6/2009 | Stad et al. |
| 2009/0312804 A1 | 12/2009 | Gamache et al. |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0093022 A1 | 4/2011 | Runco et al. |
| 2011/0144695 A1 | 6/2011 | Rosenberg et al. |
| 2011/0208254 A1 | 8/2011 | Villa et al. |
| 2012/0029571 A1 | 2/2012 | Schwab et al. |
| 2012/0143265 A1 | 6/2012 | Biedermann et al. |
| 2012/0191144 A1 | 7/2012 | Peultier et al. |
| 2012/0203291 A1 | 8/2012 | Boulaine |
| 2012/0253413 A1 | 10/2012 | Runco et al. |
| 2013/0018419 A1 | 1/2013 | Rezach et al. |
| 2013/0066385 A1 | 3/2013 | Benoist |
| 2013/0079826 A1 | 3/2013 | Simonson |
| 2013/0085534 A1 | 4/2013 | Hainard et al. |
| 2013/0123854 A1 | 5/2013 | Kondrashov et al. |
| 2014/0012337 A1 | 1/2014 | Biedermann et al. |
| 2014/0018858 A1 | 1/2014 | Laeng et al. |
| 2014/0074106 A1 | 3/2014 | Shin |
| 2014/0094858 A1 | 4/2014 | Picetti et al. |
| 2014/0114363 A1 | 4/2014 | Stevenson et al. |
| 2014/0148865 A1 | 5/2014 | Hennard et al. |
| 2014/0163625 A1 | 6/2014 | Meyer et al. |
| 2014/0180298 A1 | 6/2014 | Stevenson et al. |
| 2014/0276896 A1 | 9/2014 | Harper |
| 2014/0277160 A1 | 9/2014 | Ziolo |
| 2014/0277170 A1 | 9/2014 | Barett et al. |
| 2014/0277206 A1 | 9/2014 | Reitblat et al. |
| 2014/0296862 A1 | 10/2014 | Stad et al. |
| 2014/0311264 A1 | 10/2014 | Black et al. |
| 2014/0316475 A1 | 10/2014 | Parikh et al. |
| 2015/0057707 A1 | 2/2015 | Barms et al. |
| 2015/0066042 A1 | 3/2015 | Cummins et al. |
| 2015/0100097 A1 | 4/2015 | Barms |
| 2015/0100098 A1 | 4/2015 | Moore |
| 2015/0105832 A1 | 4/2015 | Gleason et al. |
| 2015/0112397 A1 | 4/2015 | Petit |
| 2015/0173803 A1 | 6/2015 | Droulout |
| 2015/0182265 A1 | 7/2015 | Biedermann et al. |
| 2015/0196328 A1 | 7/2015 | Hirschl et al. |
| 2015/0201971 A1 | 7/2015 | Gaines et al. |
| 2015/0257798 A1 | 9/2015 | Biedermann et al. |
| 2015/0359568 A1 | 12/2015 | Rezach |
| 2016/0022317 A1 | 1/2016 | Kraus |
| 2016/0066967 A1 | 3/2016 | Jackson et al. |
| 2016/0151093 A1 | 6/2016 | Barry et al. |
| 2016/0242825 A1 | 8/2016 | Simpson et al. |
| 2017/0265901 A1 | 9/2017 | Hawkins et al. |
| 2017/0333087 A1 | 11/2017 | Lee et al. |
| 2017/0333088 A1 | 11/2017 | Lee et al. |
| 2018/0014858 A1 | 1/2018 | Biester et al. |
| 2018/0161073 A1 | 6/2018 | Lee et al. |

(56) References Cited

U.S. PATENT DOCUMENTS

| | | |
|---|---|---|
| 2018/0185072 A1 | 7/2018 | Rubin et al. |
| 2018/0228518 A1 | 8/2018 | Carruth et al. |
| 2018/0280062 A1 | 10/2018 | Lee et al. |
| 2019/0117280 A1 | 4/2019 | Avidano et al. |
| 2019/0193541 A1 | 6/2019 | Takeda |
| 2020/0297395 A1 | 9/2020 | Schmura et al. |
| 2021/0059725 A1 | 3/2021 | Avidano et al. |

FOREIGN PATENT DOCUMENTS

| | | |
|---|---|---|
| DE | 29806563 U1 | 6/1998 |
| EP | 0 948 939 A2 | 10/1999 |
| EP | 1 574 175 A1 | 9/2005 |
| EP | 1 648 320 A2 | 4/2006 |
| EP | 1 796 564 A1 | 6/2007 |
| EP | 2004079 A2 | 12/2008 |
| FR | 2677242 A1 | 12/1992 |
| FR | 2680314 A1 | 2/1993 |
| FR | 2729291 A1 | 7/1996 |
| WO | 96/021396 A1 | 7/1996 |
| WO | 02080787 A3 | 4/2003 |
| WO | 03028566 A1 | 4/2003 |
| WO | 2005/006948 A2 | 1/2005 |
| WO | 2005058173 A1 | 6/2005 |
| WO | 2006/020443 A1 | 2/2006 |
| WO | 2010045301 A1 | 4/2010 |

\* cited by examiner

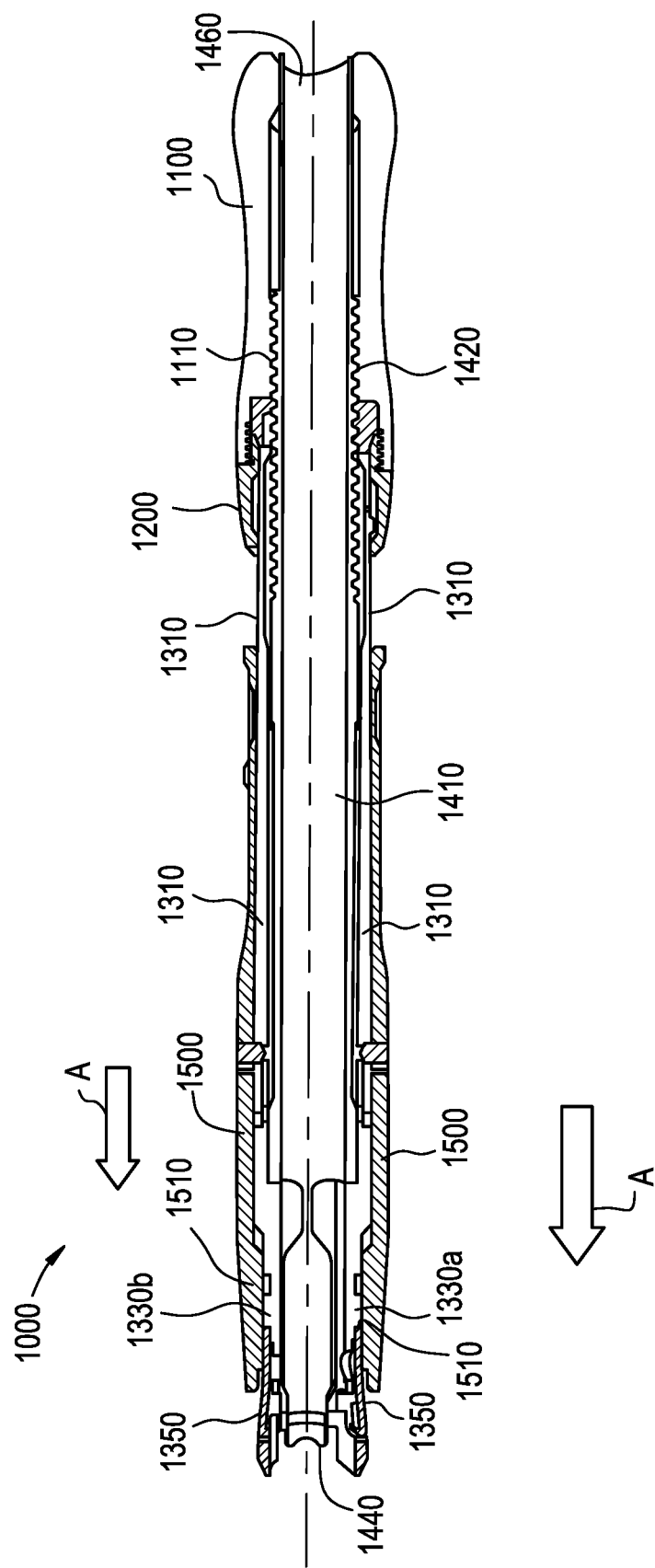

ROD REDUCERS AND RELATED METHODS

RELATED APPLICATIONS

This application is related to commonly owned U.S. Design patent application Ser. No. 29/684,449, entitled "KERRISON ROD REDUCER," and U.S. Utility patent application Ser. No. 16/360,193, entitled "ROD REDUCERS AND RELATED METHODS," both concurrently filed on Mar. 21, 2019. The entire contents of these applications are incorporated herein by reference.

FIELD

The present disclosure relates generally to spinal fixation systems, and more particularly to rod reducing devices and related methods of using rod reducing devices.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument can hold the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws can include a threaded shank that is adapted to be threaded into a vertebra, and a head portion having a rod-receiving element, usually in the form of a U-shaped slot formed in the head. A set-screw, plug, or similar type of closure mechanism can be used to lock the fixation rod into the rod-receiving portion of the pedicle screw. In use, the shank portion of each screw can be threaded into a vertebra and, once properly positioned, a fixation rod can be seated through the rod-receiving portion of each screw and the rod can be locked in place by tightening a cap or similar type of closure mechanism to securely interconnect each screw and the fixation rod.

While current spinal fixation systems have proven effective, difficulties have been encountered in seating or positioning rods in the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod reducer is often required in order to grasp the head of an anchoring device or other spinal implant and reduce the rod into the rod-receiving portion of the implant.

There remains a continued need for improved rod reducers and methods for seating a spinal rod in a rod-receiving portion of one or more spinal implants.

SUMMARY

Various embodiments are provided herein of a rod reducer and related methods of using the disclosed rod reducers for holding a spinal implant and seating a fixation rod in a rod-receiving portion of the spinal implant. The disclosed rod reducers can also be configured for applying a set screw or other closure mechanism to secure the rod within the rod-receiving portion of the spinal implant. The disclosed embodiments can be easy to use, not require significant force to operate, and be efficient, thereby reducing the time and expense necessary to perform spinal surgery. The disclosed rod reducers can be readily dissembled, thereby making these surgical instruments easy to clean and sterilize.

In one aspect, a Kerrison-style rod reducer or other surgical instrument is provided that can include a gripping assembly having a proximal end and a distal end, a rod reducing assembly having a proximal end and a distal end, a first lever, and a second lever. The distal end of the gripping assembly can be configured to hold a spinal implant. The distal end of the rod reducing assembly can be configured to engage a rod. The first lever can be pivotally coupled to the proximal end of the gripping assembly. The second lever can be pivotally coupled to the first lever and the proximal end of the rod reducing assembly. Movement of the first lever and the second lever towards one another can cause the first and second levers to pivot about the proximal end of the gripping assembly. Movement of the first and second lever towards one another can also cause the rod reducing assembly to translate distally relative to the gripping assembly, thereby pushing a rod distally into a rod-receiving portion of a spinal implant held by the gripping assembly. The surgical instrument described herein can include any of a variety of additional or alternative features, all of which are considered within the scope of the present disclosure. For example, in some embodiments, the surgical instrument can be a Kerrison-style or pistol-grip rod reducer.

By way of further example, the rod reducing assembly can slide distally over the distal end of the gripping assembly. The distal end of the gripping assembly can include one or more cantilevered gripping elements configured to engage a portion of a spinal implant when the distal end of the rod reducing assembly slides distally over the distal end of the gripping assembly. The rod reducing assembly can translate distally with a pivoting motion that is offset by the first and second levers pivoting about the proximal end of the gripping assembly.

In some embodiments, the proximal end of the rod reducing assembly can be pivotally coupled to the second lever by a pin that extends across a cavity defined at the proximal end of the rod reducing assembly. The pin can have a cross-sectional profile configured to pivotally couple the proximal end of the rod reducing assembly to the second lever when the pin is rotated to a first position and to decouple the proximal end of the rod reducing assembly from the second lever when the pin is rotated to a second position.

In some embodiments, the surgical instrument can include a lock/release mechanism. The lock/release mechanism can include the pin fixedly coupled to a lever disposed externally at the proximal end of the rod reducing assembly. The pin can be rotated into the second position when the third lever is manually rotated in a first rotational direction. The lock/release mechanism can further include a torsion spring configured to oppose rotation of the third lever in the first rotational direction and thereby bias the pin in the first position.

In some embodiments, the gripping assembly can include a first elongate beam extending proximally from a distal inner tubular body configured to hold a spinal implant. The rod reducing assembly can include a second elongate beam extending proximally from a distal outer tubular body. The outer tubular body can be slidably disposed around at least a portion of the inner tubular body of the gripping assembly. The outer tubular body can define a distal-facing surface configured to engage a rod. The inner tubular body of the gripping assembly can include one or more gripping elements configured to engage the spinal implant in response to the outer tubular body of the rod reducing assembly translating distally over the inner tubular body. The inner tubular body of the gripping assembly can be laterally offset from the first elongate beam of the gripping assembly. The outer tubular body of the rod reducing assembly can be laterally offset from the second elongate beam of the rod reducing assembly. The inner tubular body of the gripping assembly can define a second longitudinal passageway through which a fastening mechanism can be deployed to secure a rod seated in a rod-receiving portion of a spinal implant.

In another aspect, a method is provided for reducing a rod into a rod-receiving portion of a spinal implant. The method can include positioning a surgical instrument that includes a gripping assembly, a rod reducing assembly, a first lever and a second lever, such that a spinal implant having a rod-receiving portion is held at a distal end of the gripping assembly. The first lever can be pivotally coupled to a proximal end of the gripping assembly and the second lever can be pivotally coupled to the first lever and a proximal end of the rod reducing assembly. The method can further include causing the first and second levers to pivot about the proximal end of the gripping assembly and causing the rod reducing assembly to translate distally relative to the gripping assembly by moving the first lever and the second lever towards one another, thereby pushing a rod into the rod-receiving portion of the spinal implant held by the gripping assembly.

As with the aspects and embodiments described above, a number of additional or alternative features can be included that are considered within the scope of the present disclosure. For example, in some embodiments, the rod reducing assembly can slide distally over the distal end of the gripping assembly. The rod reducing assembly can translate distally with a pivoting motion that is offset by the first and second levers pivoting about the proximal end of the gripping assembly. One or more cantilevered gripping elements of the gripping assembly can engage a portion of a spinal implant when the distal end of the rod reducing assembly slides distally over the distal end of the gripping assembly. By way of further example, in some embodiments, the method can further include deploying a fastening mechanism through a passageway defined at the distal end of the gripping assembly to secure the rod in the rod-receiving portion of the spinal implant.

In another aspect, an inline-style rod reducer or other surgical instrument is provided that can include a handle, a gripping assembly, a rod reducing component, and a locking sleeve. The gripping assembly can extend distally from the handle and have multiple distally-extending fingers configured to hold a spinal implant. The rod reducing component can be disposed within a longitudinal passageway defined at least partially through the handle and the gripping assembly, such that the rod reducing component is moveably coupled to the handle. The locking sleeve can be slidably disposed around a portion of the gripping assembly, such that the locking sleeve can be distally advanced over the distally-extending fingers to couple the gripping assembly to the spinal implant. The rod reducing component can translate distally in response to a rotation of the handle in a first direction to push a rod into a rod receiving portion of the spinal implant held by the gripping assembly.

As with the aspects and embodiments described above, a number of additional or alternative features can be included that are considered within the scope of the present disclosure. For example, in some embodiments, the rod reducing component can move proximally in response to a rotation of the handle in a second direction to disengage a distal end of the rod reducing component from the rod. The rod reducing component can include a tubular shaft having one or more distally-extending fingers with each of the distally-extending fingers defining a rod-engaging surface. In some embodiments, the tubular shaft of the rod reducing component can include a threaded portion for moveably coupling the rod reducing component to the handle. By way of further example, in some embodiments, the surgical instrument can further include a handle collar configured to loosely couple a proximal end of the gripping assembly to a distal end of the handle. The rod reducing component can define a longitudinal passageway through which a fastening mechanism can be deployed to secure a rod seated in a rod-receiving portion of the spinal implant.

In another aspect, a method is provided for reducing a rod into a rod-receiving portion of a spinal implant. The method can include positioning a surgical instrument that comprises a handle, a gripping assembly, a rod reducing component, and a locking sleeve, such that a spinal implant having a rod-receiving portion is held by multiple distally-extending fingers of the gripping assembly. The gripping assembly can extend distally from the handle. The rod reducing component can be disposed within a longitudinal passageway defined at least partially through the handle and the gripping assembly. The locking sleeve can be slidably disposed around a portion of the gripping assembly. The method can further include distally advancing the locking sleeve over the fingers of the gripping assembly to couple the gripping assembly to the spinal implant and rotating the handle in a first direction to cause the rod reducing component to translate distally and push a rod into the rod-receiving portion of the spinal implant held by the gripping assembly.

As with the aspects and embodiments described above, a number of additional or alternative features can be included that are considered within the scope of the present disclosure. For example, in some embodiments, the method can further include proximally translating the rod reducing component by rotating the handle in a second direction to disengage the distal end of the rod reducing component from the rod. The method can further include deploying a fastening mechanism through a longitudinal passageway defined between a proximal end and a distal end of the rod reducing component to secure a rod seated in a rod-receiving portion of the spinal implant.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 6B is a detailed side, cross-sectional view of the rod reducer of FIG. 5A.

DETAILED DESCRIPTION

Figure 1A:
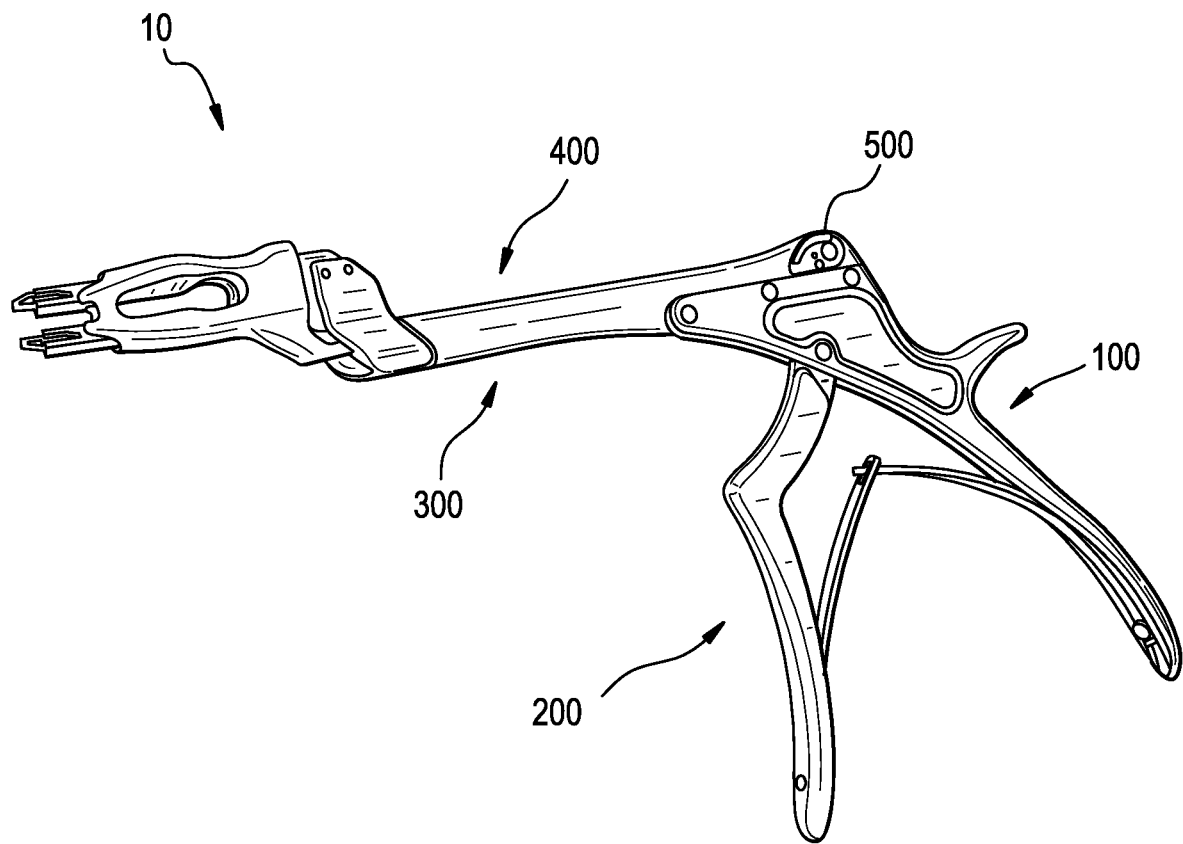
FIG. 1A is a perspective view of one exemplary embodiment of a Kerrison-style rod reducer.
Figure 1B:
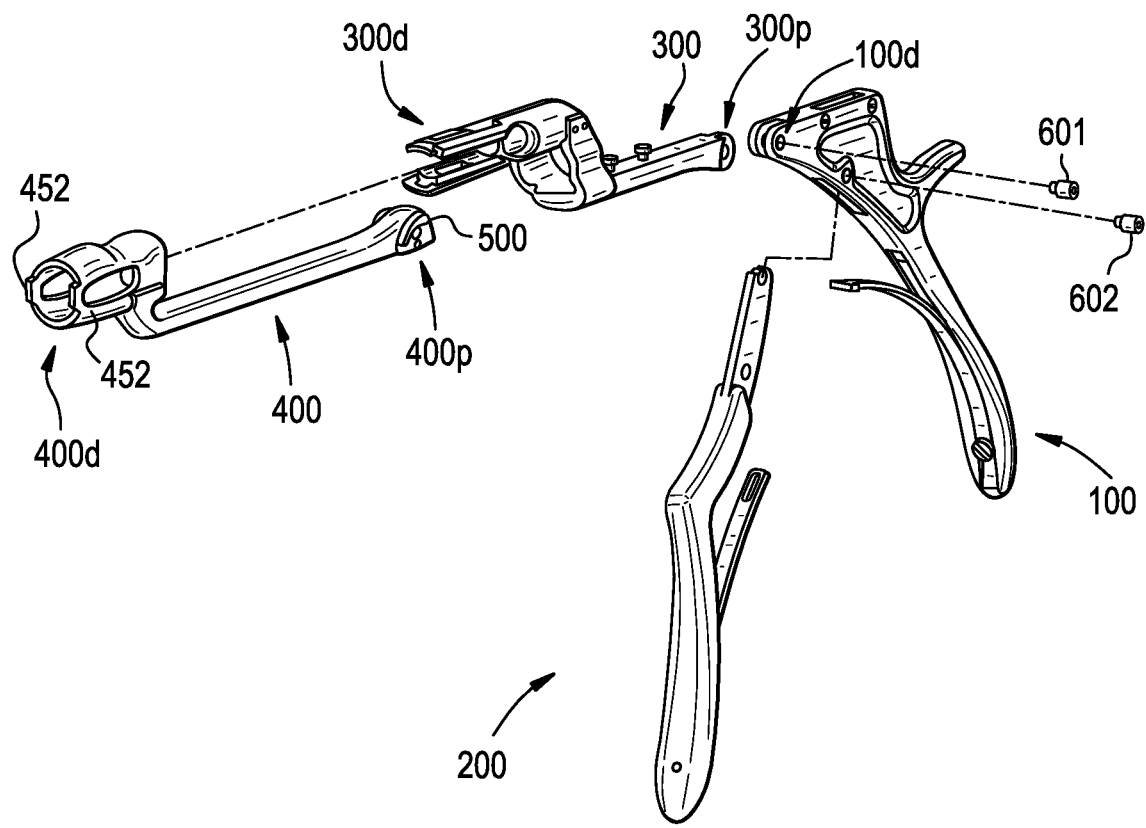
FIG. 1B is a perspective exploded view of components of the rod reducer of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Various embodiments are provided herein of a rod reducer and related methods of using the disclosed rod reducers for holding a spinal implant and seating a fixation rod in a rod-receiving portion of the spinal implant. The disclosed rod reducers can also be configured for applying a set screw or other closure mechanism to secure the rod within the rod-receiving portion of the spinal implant. The disclosed embodiments can be easy to use, not require significant force to operate, and be efficient, thereby reducing the time and expense necessary to perform spinal surgery. The disclosed rod reducers can be readily dissembled, thereby making these surgical instruments easy to clean and sterilize.

In some aspects, a Kerrison-style or pistol-grip rod reducer is disclosed. The Kerrison style rod reducers can be particularly advantageous for some clinical applications, including but not limited to quick surgical procedures that may require smaller, less forceful rod reductions. During such procedures, the Kerrison-style reducer can be operated to engage an implant construct and lock the reducer onto the implant construct while concurrently reducing the rod into the implant construct (e.g., about 10 millimeters). Further, the reducer can permit a user to lock the rod into the implant construct while the reducer holds the rod in place. Once the rod is locked to the implant construct, the reducer can be disengaged from the implant construct, thereby allowing the same or similar operations to be repeated on another implant construct. An advantage of such rod reducers is the speed at which rod reduction can be achieved, e.g., allowing a surgeon or other user to rapidly move between components of an implant construct (e.g., bone anchors inserted into multiple vertebral levels, etc.) to perform any required reduction and/or locking.

As discussed in more detail below, the Kerrison-style rod reducer can lock onto an implant construct during an initial actuation of a pair of levers. For example, as the levers are actuated and moved towards one another, a distal tubular body of a rod reducing assembly can translate over one or more gripping elements of a gripping assembly. In response, the gripping elements can be deflected into corresponding mating features of the implant construct, thereby achieving a positive lock onto the implant construct. The Kerrison-style rod reducer can concurrently achieve rod reduction through continued actuation of the levers which causes the distal tubular body of the rod reducing assembly to push a rod into the implant construct held by the gripping assembly.

In some aspects, an inline-style rod reducer is disclosed. The inline rod reducer can be particularly advantageous for some clinical applications, including but not limited to surgical procedures that may require greater, more forceful rod reductions. As discussed in more detail below, the inline reducer can lock onto an implant separately from a rod reduction process. For example, as discussed below, the inline reducer can include, among other components, a locking sleeve that can be independently translated distally and provide tactile, audible, and/or visual confirmation of a positive lock onto the implant construct. Once locked, the inline-style rod reducer can achieve rod reduction through actuation of a threaded coaxial mechanism that provides an enhanced mechanical advantage. The enhanced mechanical advantage, in combination with the coaxial nature of the threaded mechanism, can allow the inline reducer to have significant reduction capability. Thus, in some surgical procedures, the inline-style rod reducer can be operated to engage an implant construct, lock the reducer onto the implant construct, reduce a rod into the implant (e.g., about 20 mm), permit a user to lock the rod into the implant construct, e.g., using a set screw, disengage from the implant construct, and repeat the same or similar operations to reduce the rod into another implant construct.

An indicated above, the inline-style rod reducer can lock onto an implant before a rod reduction process starts. This feature can provide a surgeon with a "hands free" option to lock multiple inline reducers onto respective implant constructs before effecting a rod reduction process. Once locked, the inline rod reducers can be left free-standing without user input to maintain their position or degree of rod reduction, and they can be individually operated to reduce or partially reduce a rod into each of the respective implants, thereby allowing a surgeon to sequentially effect the overall reduction process without disengaging and reengaging a reducer to different implants. In some embodiments, the inline reducers can serve as temporary rod locks until the surgeon is satisfied with the overall reduction process. Once the rod is fully reduced into the implant constructs, the rod can be locked into the respective implant constructs by applying a set screw or other fixation device through a lumen formed in each reducer.

FIGS. 1A-1F are schematic illustrations of one exemplary embodiment of a rod reducer 10. The rod reducer 10 is a Kerrison- or pistol-grip-style surgical instrument that includes a first lever 100, a second lever 200, a gripping assembly 300, a rod reducing assembly 400, and a lock/release mechanism 500. As described in more detail below and shown in FIG. 1B, the gripping assembly 300 has a proximal end 300p and a distal end 300d. The distal end 300d of the gripping assembly 300 can be configured to receive and hold a spinal implant, e.g., bone anchors, hooks, pedicle screw assemblies, and the like. The rod reducing assembly 400 has a proximal end 400p and a distal end 400d. The distal end 400d of the rod reducing assembly 400 can be configured to push a rod into a rod-receiving portion of the implant held by the gripping assembly 300. The first lever 100 can be pivotally coupled to the proximal end 300p of the gripping assembly 300 by a first pin 601. The second lever 200 can be pivotally coupled to the first lever 100 by a second pin 602. Additionally, the second lever 200 can be pivotally coupled to the proximal end 400p of the rod reducing assembly 400 by the lock/release mechanism 500.

As described in more detail below with respect to FIGS. 2A, 2B, and 2C, moving the first and second levers 100 and 200 towards one another can cause the levers to pivot about or relative to the proximal end 300p of the gripping assembly 300. Additionally, when the first and second levers 100 and 200 are moved towards one another, the rod reducing assembly 400 can move distally relative to the gripping assembly 300 such that the distal end 400d of rod reducing assembly can push a rod distally into a rod-receiving portion of a spinal implant held by the gripping assembly. In some embodiments, the distal end 400d of the rod reducing assembly 400 can form a rigid tube or sleeve around the distal end 300d of the gripping assembly 300 such that one or more gripping elements can lock onto or otherwise securely couple to the implant as the rod reducing assembly 400 is distally advanced over the gripping assembly. The disclosed rod reducer 10 can be used to rapidly reduce and secure a rod into spinal implants across multiple vertebral levels. Further, the various components 100, 200, 300, and 400 can be dissembled to better clean and sterilize the rod reducer 10 after use.

Figure 1C:
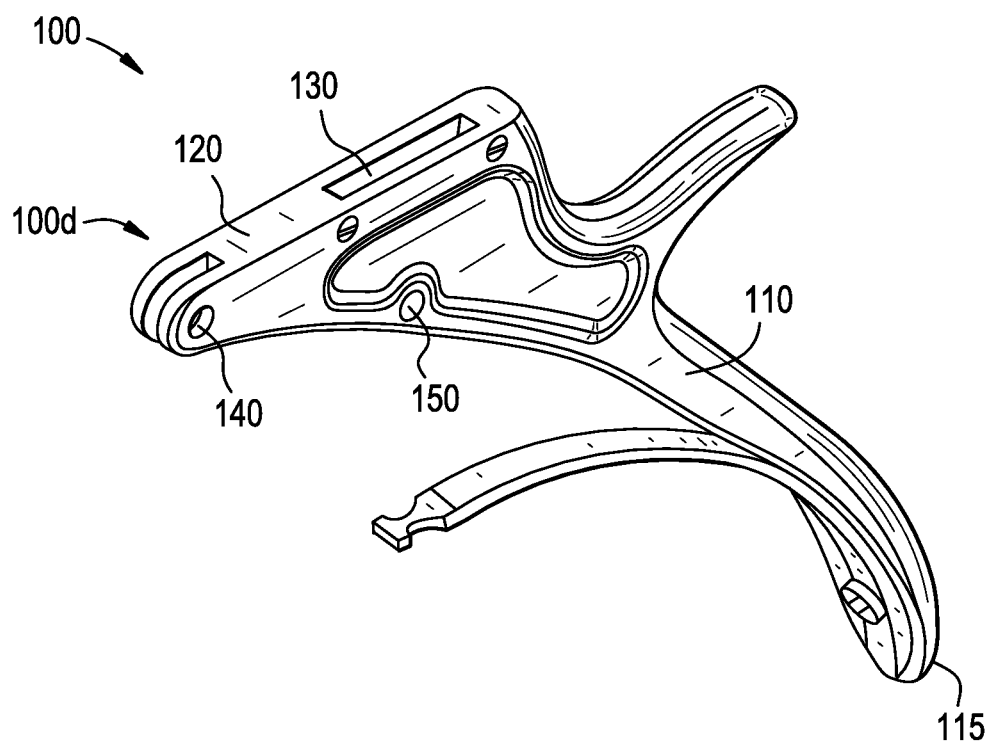
FIG. 1C is a perspective view of one exemplary embodiment of a first lever of the embodiment rod reducer of FIG. 1A.

As shown in FIG. 1C, the first lever 100 can include a body 110 having a substantially flat end portion 120. The body 110 can have any ergonomic or desired shape configured to fit a user's hand. For example, as shown in the illustrated embodiment, the body 110 of the lever 100 can have a cantilevered shape that projects from the flat end portion 120 to a tapered end portion 115. The flat end portion 120 of the lever 100 serves as a resting platform for the proximal end 400p of the rod reducing assembly 400. The body 110 of the lever 100 can define an open-ended slot 130 through which the second lever 200 can be received and pivotally couple to the first lever 100. The body 110 of the first lever 100 can define a first through bore 140 that receives a first pin 601 (see FIG. 2A) for pivotally coupling the distal end 100d of the first lever 100 to the proximal end 300p of the gripping assembly 300. The body 110 of the lever 100 can define a second through bore 150 that extends transversely through the slot 130 to receive a second pin 602 (see FIG. 2A) for pivotally coupling the first lever 100 to the second lever 200. The pins 601 and 602 can be welded or threaded to allow disassembly of the respective components, e.g., for cleaning purposes.

Figure 1D:
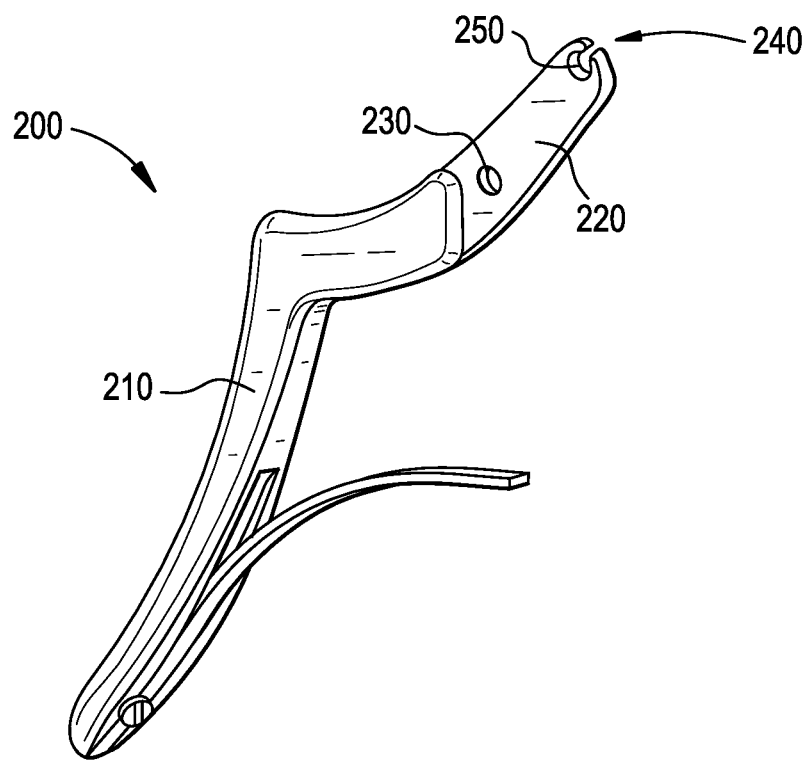
FIG. 1D is a perspective view of one exemplary embodiment of a second lever of the embodiment rod reducer of FIG. 1A.

As shown in FIG. 1D, the second lever 200 can include an elongate body 210 having an end portion 220 that is received within the open-ended slot 130 of the first lever 100. The end portion 220 of the lever 200 can define a through bore 230 that receives the pin 602 (see FIG. 2A) for pivotally coupling the second lever 200 to the first lever 100 within the slot 130. The tip 240 of the second lever 200 can be exposed through the open-ended slot 130 at the flat end portion 120 of the first lever 100. The tip 240 of the second lever 200 can define a notch 250 that pivotally couples the second lever to the lock/release mechanism 500 disposed at the proximal end 400p of the rod reducing assembly 400 (see FIG. 2A). As described in more detail below with respect to FIGS. 2A-2C, when a user manipulates the levers 100 and 200 such that they pivot about the pin 602 and move towards one another, the pivot coupling of the first lever 100 to the gripping assembly 300 by the pin 601 allows the levers 100 and 200 to pivot together about the proximal end 300p of the gripping assembly 300.

Figure 1E:
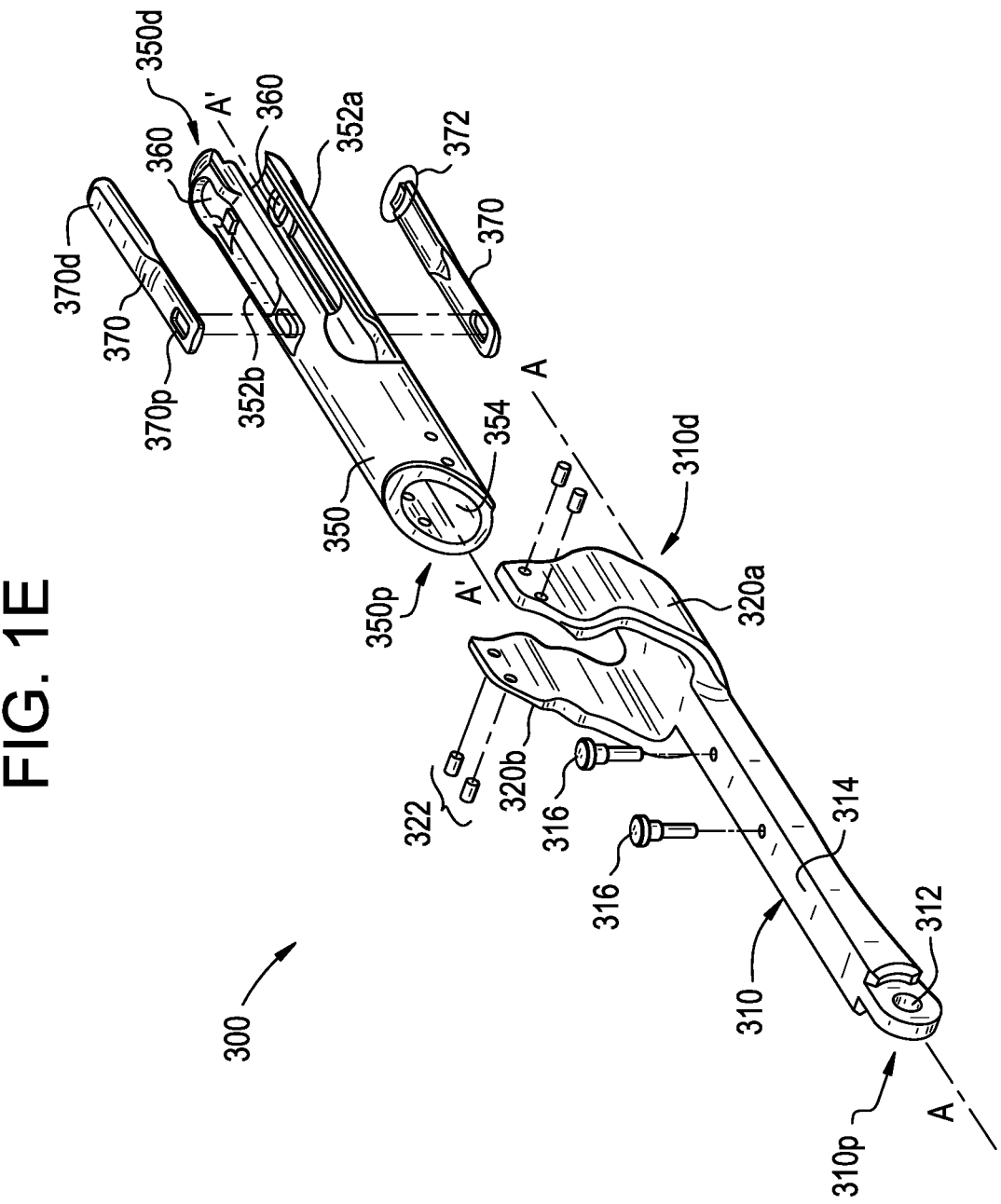
FIG. 1E is a perspective exploded view of one exemplary embodiment of a gripping assembly of the embodiment rod reducer of FIG. 1A.

As shown in FIG. 1E, the gripping assembly 300, which is separate but pivotally coupled to the first lever 100, can include an elongate beam 310 defining a proximal-distal axis A-A of the reducer 10. The beam 310 extends proximally from a distal tubular body 350 for receiving and holding a spinal implant. The beam 310 has a substantially flat bearing surface 314 that extends between a proximal end 310p and a distal end 310d of the beam 310. The bearing surface 314 of the beam 310 can provide a platform on which an opposing bearing surface of the rod reducing assembly 400 can slide back-and-forth. In some embodiments, the beam 310 can include one or more guide pins 316 or other protruding structures that dovetail or otherwise slidably engage with a counterpart slot or groove in the opposing bearing surface of the rod reducing assembly 400. A through bore 312 is defined at the proximal end 310p of the beam to receive the pin 601 for pivotally coupling the gripping assembly 300 to the distal end 100d of the lever 100.

The distal tubular body 350 of the gripping assembly 300 is configured to receive, locate, and align a spinal implant. The distal tubular body 350 has a proximal end 350p and a distal end 350d. An open-ended passageway 354 is defined between the proximal and distal ends of the tubular body 350. The passageway 354 can have dimensions (e.g., diameter, height, width, cross-sectional profile, etc.) configured to allow insertion of a set screw, plug, or other closure mechanism to fix a rod seated in an implant held by the assembly 300. The distal tubular body 350 of the assembly 300 can have any desired length. For example, the distal tubular body 350 can have a length for effectively guiding subsequent instrumentation through the cannulation, such as but not limited to a set-screw, a set-screw driver, and the like. In some embodiments, the length $L_1$ of the tubular body 350 can range from approximately 45 mm to approximately 120 mm. For example, the length $L_1$ of the tubular body 350 can be equal to approximately 70 mm.

In some embodiments, the distal tubular body 350 of the assembly 300 can include a number of nesting elements configured to receive, locate and align (sometimes referred to herein as "nest") a spinal implant. For example, the distal tubular body 350 can include a pair of distally-extending fingers 352a and 352b (collectively 352). The fingers 352 can be spaced apart to form a pocket that accommodates the size and shape of the implant. The inner surface of the fingers 352 can define one or more structural features that are configured to nest counterpart structural features of an implant. For example, in some embodiments, the one or more structural features defined in the fingers 352 can include, without limitation, ridges, grooves, protrusions, and other contoured surfaces.

In some embodiments, one or more of the distally-extending fingers 352 of the gripping assembly 300 can define a window 360 configured to expose a portion of a received implant. Each window 360 can be covered or at least partially covered by a cantilevered gripping element 370 having an elongate flexible body. The proximal end 370p of the cantilevered gripping element 370 can be fixed to an outer surface of the finger adjacent to the window 360. The cantilevered gripping element 370 can be made of an elastic material so that the distal end 370d of the gripping element 370 can be pressed into the window 360 when the rod reducing assembly 400 is advanced over the fingers 352 and retracted from the window 260 when the rod reducing assembly is proximally withdrawn from the fingers. The distal end 370d of the cantilevered gripping element 370 can define a locking feature 372 configured to engage a counterpart locking feature of the implant through the window. For example, in some embodiments, the locking feature 372 of the cantilevered gripping element 370 can include a ridge or other protrusion configured to mate with a notch, groove, or other recess defined in the outer surface of the implant. As described in more detail below with respect to FIGS. 2A-2C, the cantilevered gripping elements 370 can be configured to engage an implant as the rod reducing assembly 400 is distally advanced over the fingers 352.

In some embodiments, the distal tubular body 350 of the gripping assembly 300 can be laterally offset from the elongate beam 310 of the gripping assembly by one or more lateral support arms. For example, as shown in the illustrated embodiment of FIG. 1E, a pair of lateral support arms 320a and 320b (collectively 320) can be disposed at the distal end 310d of the elongate beam 310 and fixedly coupled to a proximal end 350p of the tubular body 350 of the gripping assembly 300. In some embodiments, the lateral support arms 320 can be fixedly coupled to the tubular body 350 of the gripping assembly 300 by welded dowel pins 322. However, a person skilled in the art with recognize that other techniques for coupling two mechanical components can be used in other embodiments. Advantages of laterally offsetting the distal tubular body 350 from the elongate beam 310 of the gripping assembly 300 can include improved user visibility and/or access to the implant through the open-ended passageway 354.

Figure 1F:
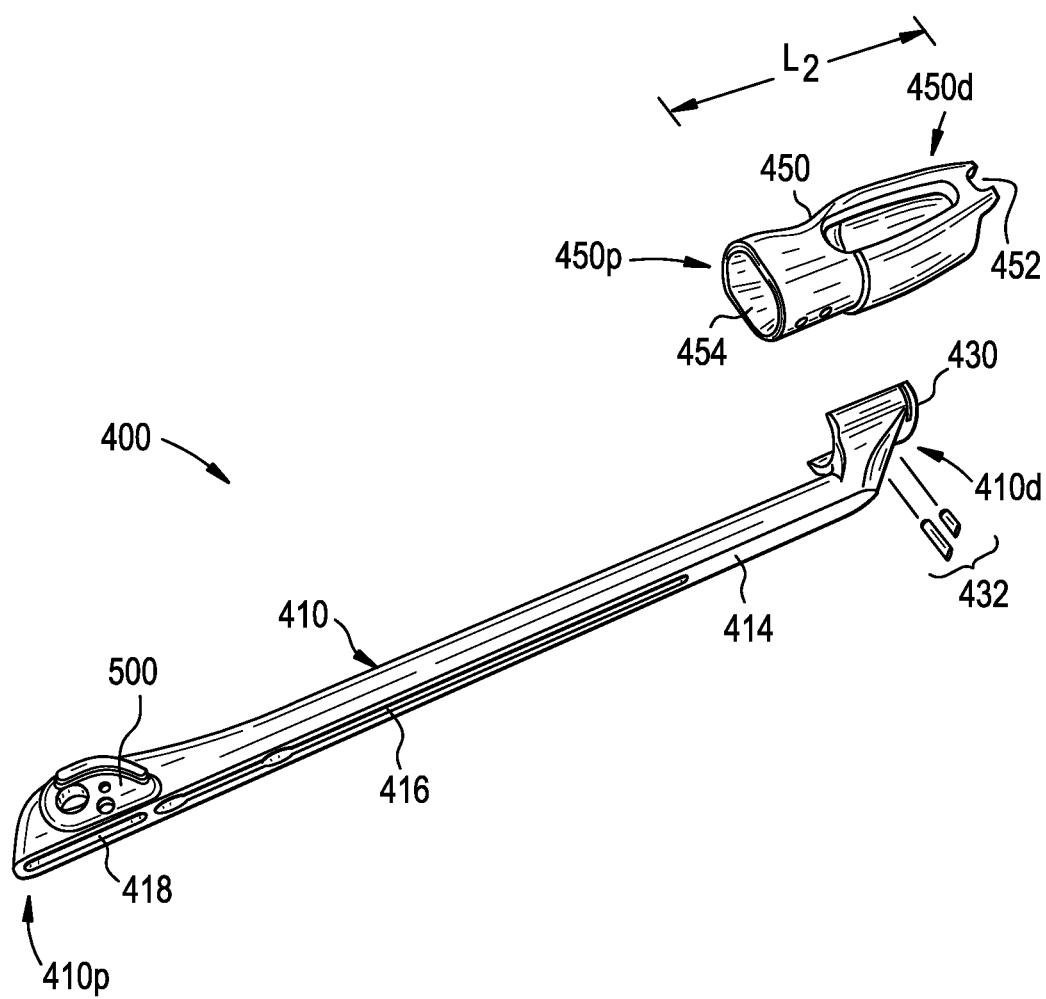
FIG. 1F is a perspective exploded view of one exemplary embodiment of a rod reducing assembly of the embodiment rod reducer of FIG. 1A.

As shown in FIG. 1F, the rod reducing assembly 400, which is separate but pivotally coupled to the second lever 200, can include an elongate beam 410 that extends proximally from a distal tubular body 450 for pushing a rod into a rod-receiving portion of an implant. The beam 410 of the assembly 400 can rest on a platform formed by the substantially flat end portion 120 of the first lever 100 and the opposing bearing surface 314 of the beam 310 of the gripping assembly 300. The beam 410 can have a substantially flat bearing surface 414 for sliding back-and-forth along the platform. The beam 410 of the rod reducing assembly 400 can include a lock/release mechanism 500 for pivotally coupling the proximal end 410p of the beam 410 to the tip 250 of the lever 200. As discussed in more detail with respect to FIGS. 3A-3D, the lock/release mechanism 500 can extend transversely through a cavity 418 that is defined at the proximal end 410p of the beam 410 and configured to receive the tip 250 of the lever 200.

In some embodiments, a slot or groove 416 can be defined in the flat bearing surface 414 of the beam 410 to dovetail with or otherwise slidably engage with the guide pins 316 protruding from the beam 310 of the gripping assembly 300. The slidable coupling of the guide pins 316 of the beam 310 and the slot 416 of the beam 410 can assist in guiding the beam 410 as it slides along the beam 310 of the assembly 300. The slidable coupling of the guide pins 316 of the beam 310 and the slot 416 of the beam 410 can also assist during assembly and disassembly of the device by guiding and locating attachment and detachment positions of the beam 410 as it slides along the beam 310 of the assembly 300.

The distal tubular body 450 of the rod reducing assembly 400 can be configured to contact and apply a distal force for pushing a rod into a rod-receiving portion of an implant. Additionally, the distal tubular body 450 can be configured to cause one or more gripping elements of the gripping assembly 300 to lock onto or otherwise securely couple to an implant. The distal tubular body 450 has a proximal end 450p and a distal end 450d. An open-ended passageway 454 can be defined between the proximal and distal ends of the tubular body 450. The passageway 454 can have dimensions (e.g. diameter, height, width, cross-sectional profile, etc.) configured to allow the distal tubular body 450 of the rod reducing assembly 400 to form a sleeve slidably disposed around the distal tubular body 350 of the gripping assembly 300. The length $L_2$ of the distal tubular body 450 of the rod reducing assembly 400 can be less than or equal to the length $L_1$ of the distal tubular body of the gripping assembly 300. In some embodiments, the length $L_2$ of the distal tubular body 450 can range from approximately 20 mm to approximately 95 mm. For example, the length $L_2$ can be equal to approximately 44 mm.

The distal end 450d of the tubular body 450 can define one or more distal-facing recessed surfaces 452 configured to engage a rod. For example, the recessed surfaces 452 can be shaped to contact and push a rod into a rod-receiving portion of an implant as the rod reducing assembly 400 is distally advanced over the gripping assembly. In some embodiments, a pair of rod-engaging recessed surfaces 452 can be defined at the distal-facing edge of the tubular body 450. In some embodiments, the rod-engaging recessed surfaces 452 can be located on one or both sides to engage the rod outside the perimeter of the implant.

In some embodiments, the distal tubular body 450 of the rod reducing assembly 400 can be laterally offset from the elongate beam 410 by a laterally-facing saddle 430 configured to coaxially align the open-ended passageway 454 of the distal tubular body 450 with the open-ended passageway 354 of the distal tubular body 350 of the gripping assembly 300. For example, the saddle 430 can be disposed at the distal end 310d of the elongate beam 410 and fixedly coupled to the proximal end 450p of the tubular body 450. In some embodiments, the saddle 430 can be fixedly coupled to the tubular body 450 of the assembly 400 by welded dowel pins 432. However, a person skilled in the art will recognize that other techniques for coupling two mechanical components can be used in other embodiments. As described in more detail below with respect to FIGS. 2A-2C, when a user manipulates the levers 100 and 200 such that they pivot about the pin 602 and move towards one another, the pivotal coupling of the second lever 100 to the rod reducing assembly 500 by the lock/release mechanism 500 causes the rod reducing assembly to translate distally relative to the gripping assembly 300, thereby pushing a rod into a rod-receiving portion of a spinal implant held by the gripping assembly.

Figure 2A:
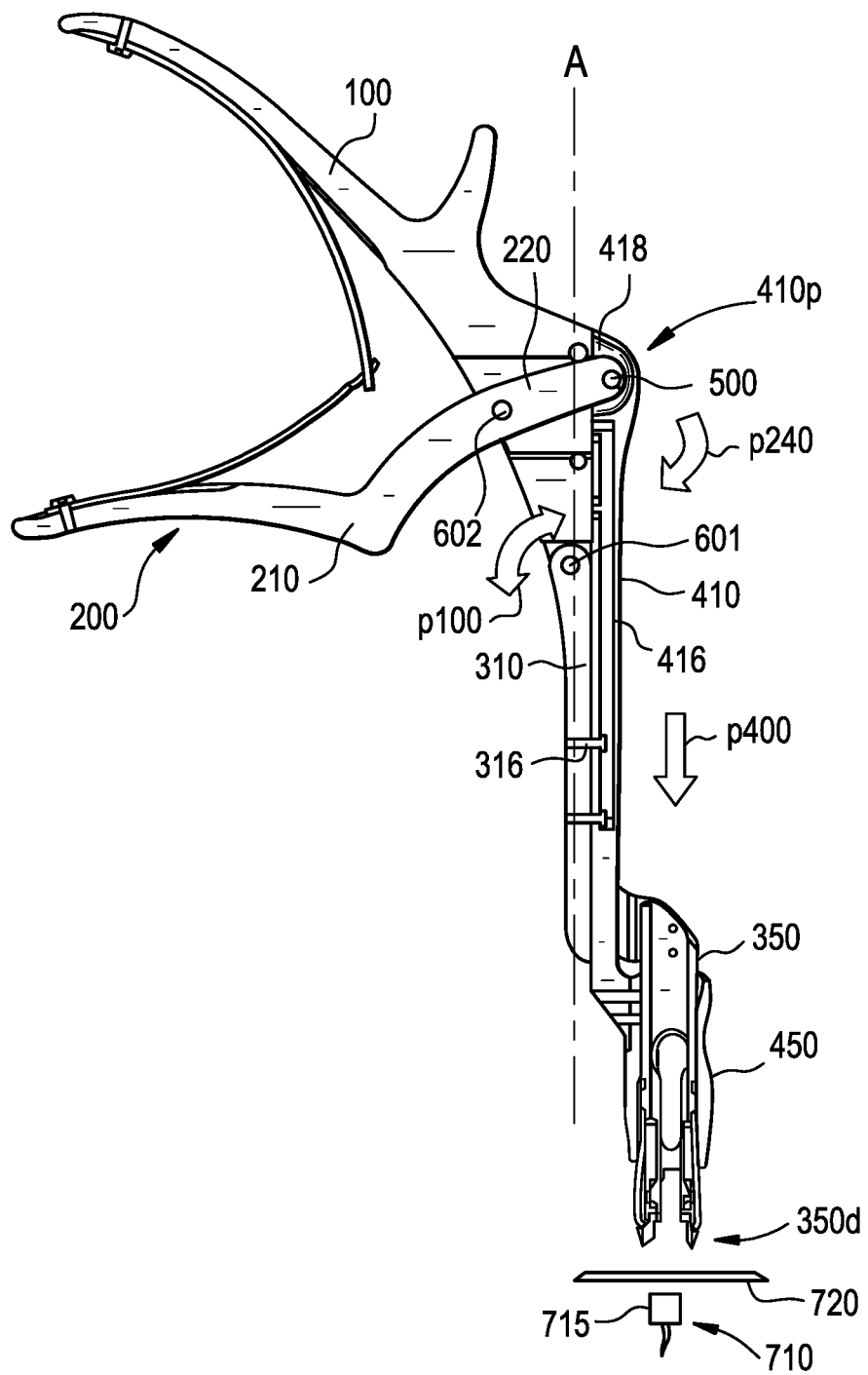
FIG. 2A is a detailed side, cross-sectional view of the embodiment rod reducer of FIG. 1A.
Figure 2B:
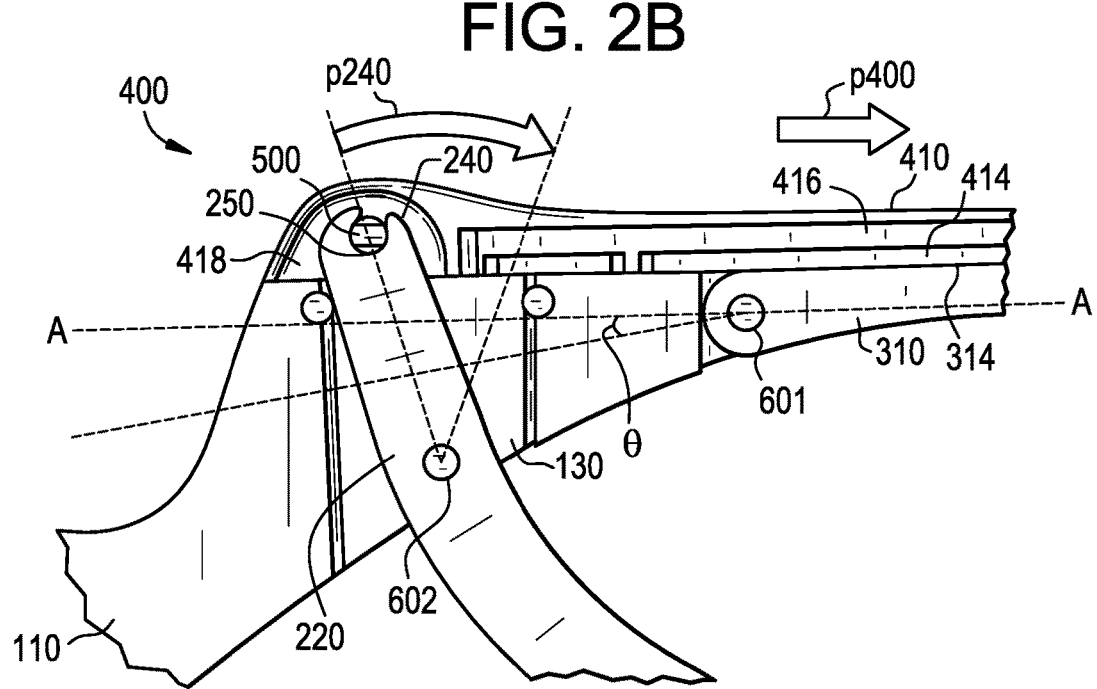
FIG. 2B is a detailed side, cross-sectional view of components of the embodiment rod reducer of FIG. 1A, the components including a first lever, a second lever, a proximal end of a rod reducing assembly, and a proximal end of a gripping assembly.
Figure 2C:
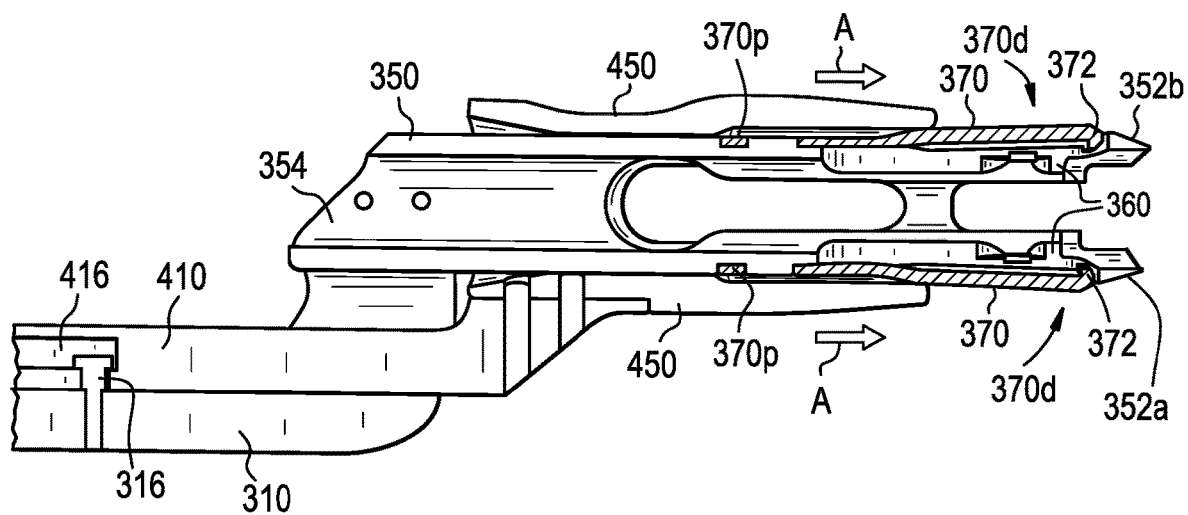
FIG. 2C is a detailed side, cross-sectional view of components of the embodiment rod reducer of FIG. 1A, the components including a distal end of a rod reducing assembly and a distal end of a gripping assembly.

FIGS. 2A-2C are cross-sectional views of the rod reducer of FIG. 1A to illustrate one exemplary method of using the rod reducer 10 to seat a rod in a rod-receiving portion of an implant. As shown in FIG. 2A, the rod reducer 10 can be positioned such that the distal tubular body 350 of the gripping assembly 300 receives, or at least partially receives, a spinal implant 710 having a rod 720 aligned within the rod-receiving portion 715. In some embodiments, the implant can be, for example, a bone anchor, hook, pedicle screw assembly, and the like.

As shown in FIGS. 2A and 2B, the first lever 100 can be pivotally coupled to the gripping assembly 300 by the pin 601. The second lever 200 can be pivotally coupled to the first lever 100 by the pin 602. The tip 240 of the second lever 200 can be pivotally coupled to the proximal end 400p of the rod reducing assembly 400 by a lock/release mechanism 500 (see FIGS. 3A-3D). In some embodiments, the lock/release mechanism 500 can be a pin itself. When the first lever 100 and the second lever 200 move towards one another, the second lever 200 can pivot about the pin 602 such that the tip 240 of the second lever moves distally along an arcuate path p240. As the tip 240 moves along the arcuate distal path p240, the lock/release mechanism 500 coupled thereto also moves along the same or a similar path, thereby causing the rod reducing assembly 400 to move distally relative to the gripping assembly 300.

However, the arcuate distal path p240 followed by the tip 240 of the second lever 200 and the lock/release mechanism 500 can cause the rod reducing assembly 400 to pivot relative to the proximal-distal axis A-A of the gripping assembly 300. To offset or at least partially offset the pivoting motion of the rod reducing assembly 400 and maintain axial alignment with the proximal-distal axis A-A of the gripping assembly, the first lever 100 can be pivotally coupled to the proximal end 300p of the gripping assembly 300 by the pin 601. As the rod reducing assembly 400 moves distally, the first lever 100 pivots back-and-forth along an arcuate path p100 relative to the pin 601 such that the first and second levers 100 and 200 pivot about or relative to the proximal end 300p of the gripping assembly 300. In some embodiments, the first lever 100 can pivot about the pin 601 through an oblique angle θ that can range from approximately 0 degrees to approximately 10 degrees relative to the proximal-distal axis A-A. For example, in the illustrated embodiment, the first lever 100 can have an angular range of motion approximately in the range of about 0 degrees to about 1.5 degrees. The angular range of motion can be related to, and a result of, the designed rod reduction maximum stroke.

By allowing the first and second levers 100, 200 to pivot, the rod reducing assembly 400 can move distally along a substantially linear path p400 in parallel with the proximal-distal axis A-A of the gripping assembly 300. In some embodiments, the guide pins 316 protruding from beam 310 of the gripping assembly 300 can dovetail or otherwise slidably couple with the slot 416 defined in the beam 410 of the rod reducing assembly 400. Thus, the guide pins 316 and the slot 416 can enforce the distal movement of the rod reducing assembly 400 along the linear path p400, resulting in the first and second levers 100 and 200 pivoting about the proximal end 300p of the gripping assembly 300 to maintain axial alignment of the respective assemblies.

As shown in FIG. 2C, as the rod reducing assembly 400 moves distally relative to the gripping assembly 300, the outer tubular body 450 of the assembly 400 can advance over the inner tubular body 350 of the assembly 300 like a sleeve. The outer tubular body 450 can advance up to or past the distal end 350d of the gripping assembly 300 to push or reduce the rod 720 into the rod-receiving portion 715 of the implant 710. For example, in some embodiments, the outer tubular body 450 can be advanced such that the rod-engaging recessed surfaces 452 at the distal end 450d of the rod reducing assembly 400 (see FIG. 1F) contact and apply a distal force on the rod 710. In some embodiments, the rod reducing assembly 400 can be configured to effect a rod reduction in a range between approximately 0 millimeters (mm) and approximately 20 mm. In some embodiments, the rod reduction can be greater than 20 mm. For example, the rod reducing assembly 400 can be configured to effect a rod reduction of approximately 10 millimeters (mm). After the rod 720 is seated within the rod-reducing portion 715 of the implant 710, a fastening mechanism, such as a set screw, can be deployed through the inner tubular body 350 of the gripping assembly 300 to fix the rod in place. In some embodiments, the outer tubular body 450 and the inner tubular body 350 can have respective lengths to achieve greater or lesser reduction capability. Alternatively or additionally, the pivot range of the first lever 100 and the second lever 200 can be increased or decreased to achieve greater or lesser reduction capability.

In some embodiments, one or more gripping elements of the gripping assembly 300 can be configured to lock onto or otherwise securely couple to the implant 710 as the outer tubular body 450 of the rod reducing assembly 400 is advanced. For example, as shown in FIG. 2C, the gripping assembly 300 can include a cantilevered gripping element 370 that covers a window 360 defined in one or more of the fingers 352. As the outer tubular body 450 is advanced over the cantilevered gripping element 370 (shown by arrows A in FIG. 2C), an inner wall of the tubular body 450 can press a distal end 370d of the cantilevered gripping element into the window 360. A locking feature 372 disposed at the distal end 370d of the gripping element 370 can mate with a counterpart locking feature of the implant 710 exposed through the window. The locking feature 372 can include a ridge or other protrusion configured to mate with a notch, groove, or other recess defined in the outer surface of the implant (not shown). In some embodiments, the cantilevered gripping element 370 can be made of an elastic material so that the distal end 370d of the gripping element 370 can retract from the window 360 when the outer tubular body 450 of the rod reducing assembly 400 is proximally withdrawn.

FIGS. 3A-3D are schematic illustrations of one exemplary embodiment of the lock/release mechanism 500 of FIG. 1A. The lock/release mechanism 500 can include a lock/release pin 510 coupled to a spring-biased lever 520 disposed externally on one or both sides at the proximal end

Figure 3A:
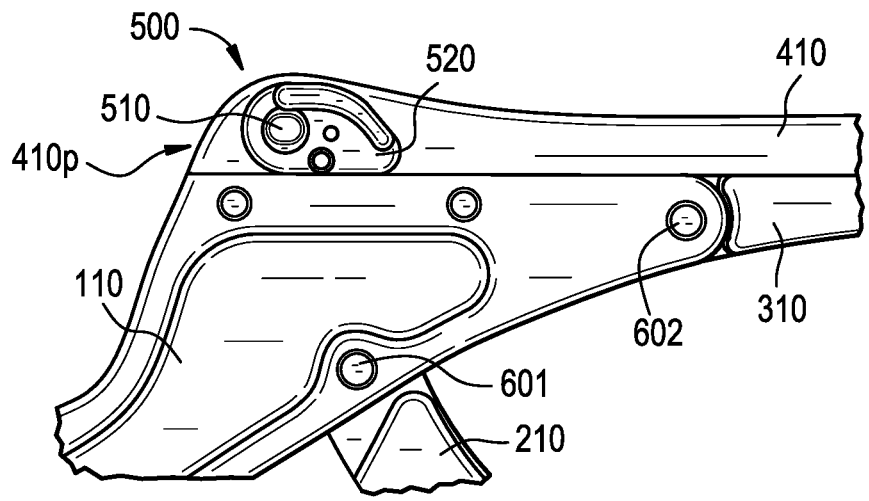
FIG. 3A is a side perspective view of components of the embodiment rod reducer of FIG. 1A, the components including one exemplary embodiment of a lock/release mechanism.
Figure 3B:
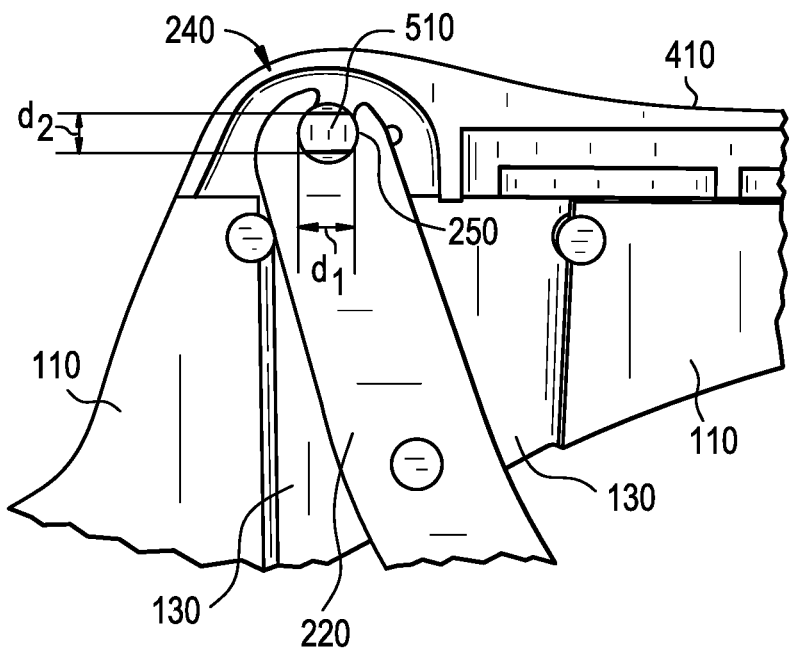
FIG. 3B is a detailed side, cross-sectional view of component of the embodiment rod reducer of FIG. 1A, the components including one exemplary embodiment of a lock/release mechanism.

400p of the rod reducing assembly 400. As shown in FIG. 3B, the lock/release pin 510 can extend transversely across a cavity 418 (see FIG. 1F) defined at the proximal end 410p of the beam 410. The lock/release pin 510 can be pivotally coupled to a notch 250 defined at the tip 240 of the lever 100 received within the cavity 418. As previously described with respect to FIGS. 2A-2C, the pivotal coupling of the lock/release pin 510 to the tip 240 of the lever 100 can cause the rod reducing assembly 400 to move distally with respect to the gripping assembly 300 in response to movement of the levers 100 and 200.

Figure 3C:
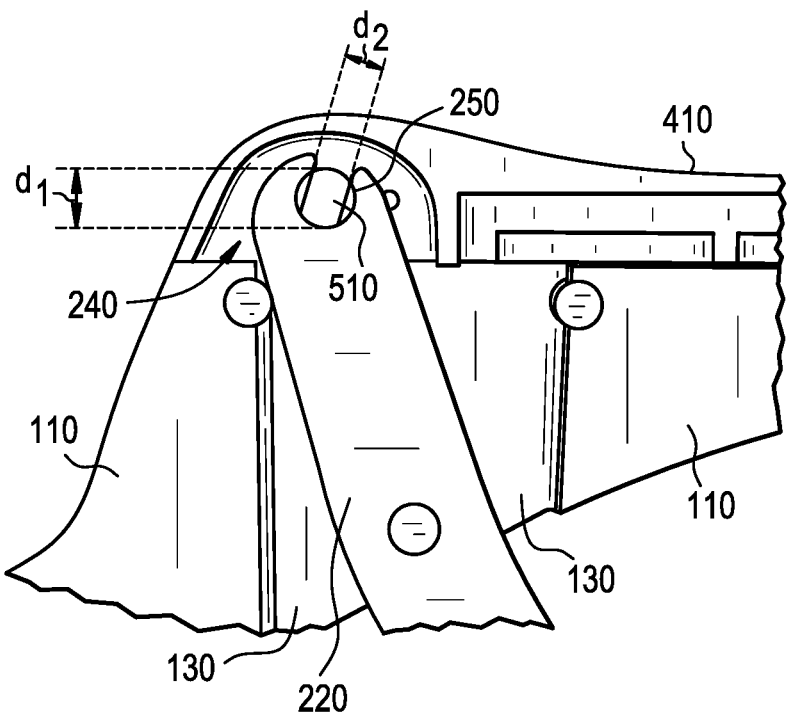
FIG. 3C is a detailed side, cross-sectional view of component of the embodiment rod reducer of FIG. 1A, the components including one exemplary embodiment of a lock/release mechanism.

In some embodiments, it can be useful to disassemble the rod reducing assembly 400 from the rest of the instrument, e.g., for cleaning purposes. To allow the rod reducing assembly 400 to be disassembled from the second lever 200, at least a portion of the lock/release pin 510 can be configured to have a cross-sectional profile that prevents decoupling of the pin 510 from the notch 250 when the pin is rotated to a locked position and allows decoupling of the pin from the notch 250 when rotated to an unlocked position. For example, as shown in FIGS. 3B and 3C, the cross-sectional profile of lock/release pin 510 can have a first dimension $d_1$ (e.g., a width) that is greater than the opening of the notch 250 and a second dimension $d_2$ (e.g., a height) that is equal to or less than the opening of the notch 250. For example, in some embodiments, the lock/release pin 510 can be a flattened cylinder of diameter $d_1$.

When the lock/release pin 510 is rotated to a locked position, as shown in FIG. 3B, the surface of the lock/release pin associated with the first dimension $d_1$ faces the opening of the notch 250 and thereby prevents the pin from exiting the notch. Conversely, as shown in FIG. 3C, when the lock/release pin 510 is rotated to an unlocked position, the surface of the lock/release pin associated with the second dimension $d_2$ faces the opening of the notch 250, thereby allowing the pin to exit the notch. In some embodiments, to facilitate rotation of the lock/release pin 510 between the locked and unlocked positions, a user can manually rotate an externally disposed lever 520 (see FIG. 3A) that is fixedly coupled to the lock/release pin. For example, the lever 520 can be rotated in counter-clockwise (or clockwise) direction to rotate the lock/release pin 510 into an unlocked position. Conversely, the lever 520 can be rotated in an opposite direction to rotate the lock/release pin 520 into the locked position.

Figure 3D:
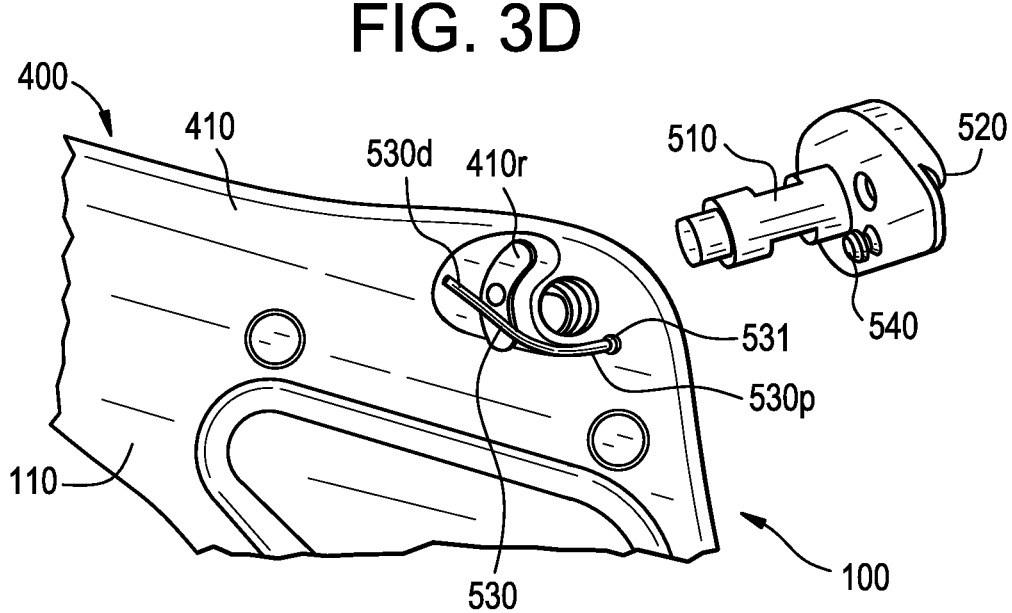
FIG. 3D is a perspective exploded view of components of the embodiment rod reducer of FIG. 1A, the components including one exemplary embodiment of a lock/release mechanism.

In some embodiments, the lever 520 of the lock/release mechanism 500 can be spring-biased to urge the lock/release pin 510 in a locked position and thereby prevent inadvertent detachment of the lock/release pin from the lever 200. For example, as shown in FIG. 3D, the lock/release mechanism 500 can include a torsion spring 530 configured to apply a bias force that opposes the rotation of the lever 520 in a direction for decoupling the pin 510. The torsion spring 530 can have a substantially linear elongate body disposed between the beam 410 of the rod reducing assembly and the lever 520. For example, in the illustrated embodiment, the torsion spring 530 can be an L-shaped leaf spring having a proximal end 530p coupled to the beam 410 (e.g., disposed within a bore 531 formed in the beam 410) and a cantilevered distal end 530d. The spring 530 can have a small diameter, e.g., approximately 0.5 mm, though other diameters are also possible. In some embodiments, the spring 530 can be made of a metal or metallic alloy, e.g., nitinol, or other suitable material.

The cantilevered end 530d of the spring 530 can be configured to apply a downward bias force on a guide post 540 that projects inwardly from the lever 510 towards the beam 410 of the assembly 400. In some embodiments, the guide post 540 can be configured to slide within a groove or other recess 410r defined in the outer surface of the beam 410 when the lever 520 is manually rotated into the unlocked position. Additionally, the upper extent 410r' and the lower extent 410r" of the recess 410r can constitute stop surfaces for the guide post 540, which can be used for providing definitive lock/unlock stroke limitations for the lock/release mechanism. The torsion spring 530 can be configured to apply a bias force for preventing inadvertent rotation of the lever 520 that can be readily overcome by, e.g., a user's application of a rotational force. Thus, although the lock/release mechanism 500 provides the ability to disassemble the rod reducing assembly 400 from the rest of the rod reducer 10, the disclosed lock/release mechanism is additionally configured to prevent accidental release of the rod reducing assembly 400 during use.

Figure 3E:
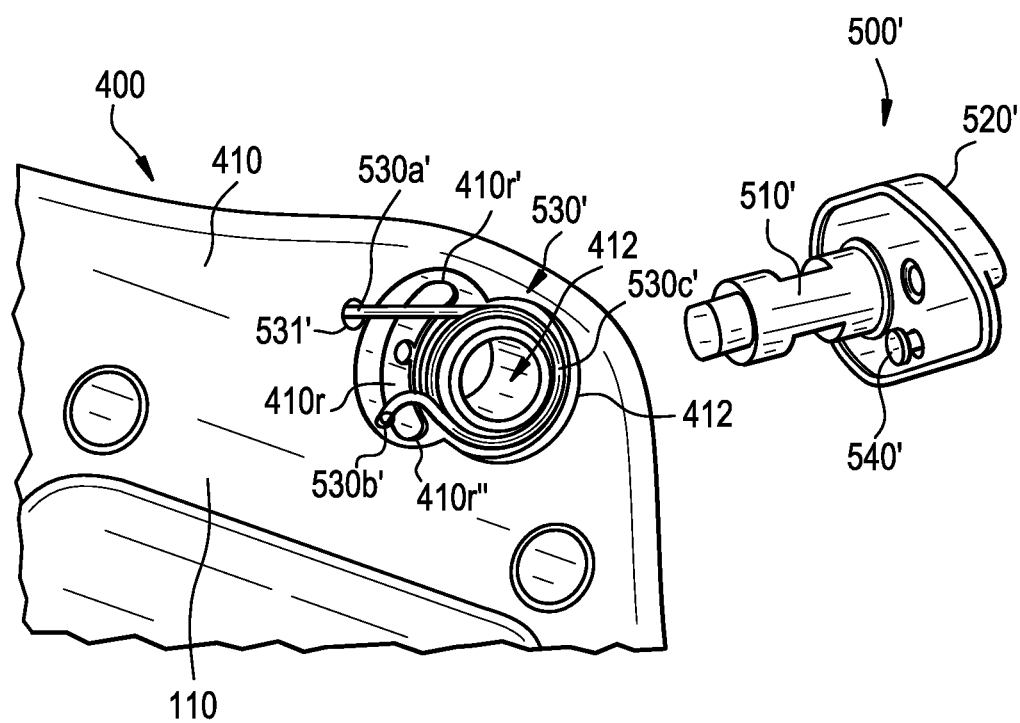
FIG. 3E is a perspective exploded view of components of the embodiment rod reducer of FIG. 1A, the components including another exemplary embodiment of a lock/release mechanism.

As shown in FIG. 3E, in some embodiments, a torsion spring 530' having a wound or coiled configuration can be used to spring bias a lock/release mechanism 500'. Advantages of the coiled spring 530' can include improved strength and/or durability. Except as indicated below and as will be readily appreciated by one having ordinary skill in the art in view of the present disclosure, the structure and operation of the lock/release mechanism 500' is substantially the same as that of the lock/release mechanism 500 described above. Accordingly, a detailed description is omitted here for the sake of brevity. It will be appreciated that the lock/release mechanism 500' can include any of the features described herein with respect to the lock/release mechanism 500.

The coiled torsion spring 530' can be attached to either or both sides at the proximal end 410p of the beam 410 of the rod reducing assembly 400. As shown in the illustrated embodiment, the coiled torsion spring 530' can have a first end 530a' coupled to the beam 410 and a free second end 530b'. The first end 530a' of the torsion spring can be fixed to a side of the beam 410 through a bore 531'. The free end 530b' of the coiled torsion spring can be shaped to latch onto the guide post 540', e.g., like a hook. A wound or coiled portion 530c' having one or more coils can extend between the first and second ends of the torsion spring 530'. The coiled portion 530c' of the spring can be disposed within a recess 412 at the proximal end 410p of the beam 410. For example, as shown in the illustrated embodiment, the recess 412 can be defined to surround a through bore 413 that receives the lock/release pin 510'. The coiled torsion spring 530' can be made of a wire or a flexible rod having a small diameter, e.g., approximately 0.5 mm, though other diameters are also possible. In some embodiments, the coiled torsion spring 530' can be made of a metal or metallic alloy, e.g., nitinol, or other suitable material.

In operation, the coiled torsion spring 530' can apply a bias force that opposes the rotation of the lever 520' in a direction for decoupling the pin 510'. For example, the free end 530b' of the coiled spring 530' can apply a downward bias force on the guide post 540'. As discussed above with respect to FIG. 3A, the guide post 540' can be configured to slide within a groove or other recess 410r defined in the outer surface of the beam 410 when the lever 520' is manually rotated into the unlocked position. Additionally, the upper extent 410r' and the lower extent 410r" of the recess 410r can constitute stop surfaces for the guide post 540', which can be used for providing definitive lock/unlock stroke limitations for the lock/release mechanism 500'. The coiled torsion spring 530' can be configured to apply a bias force for preventing inadvertent rotation of the lever 520' that can be readily overcome by, e.g., a user's application of a rotational force. Thus, although the lock/release mechanism 500' provides the ability to disassemble the rod reducing assembly 400 from the rest of the rod reducer 10, the disclosed lock/release mechanism is additionally configured to prevent accidental release of the rod reducing assembly 400 during use.

Figure 4:
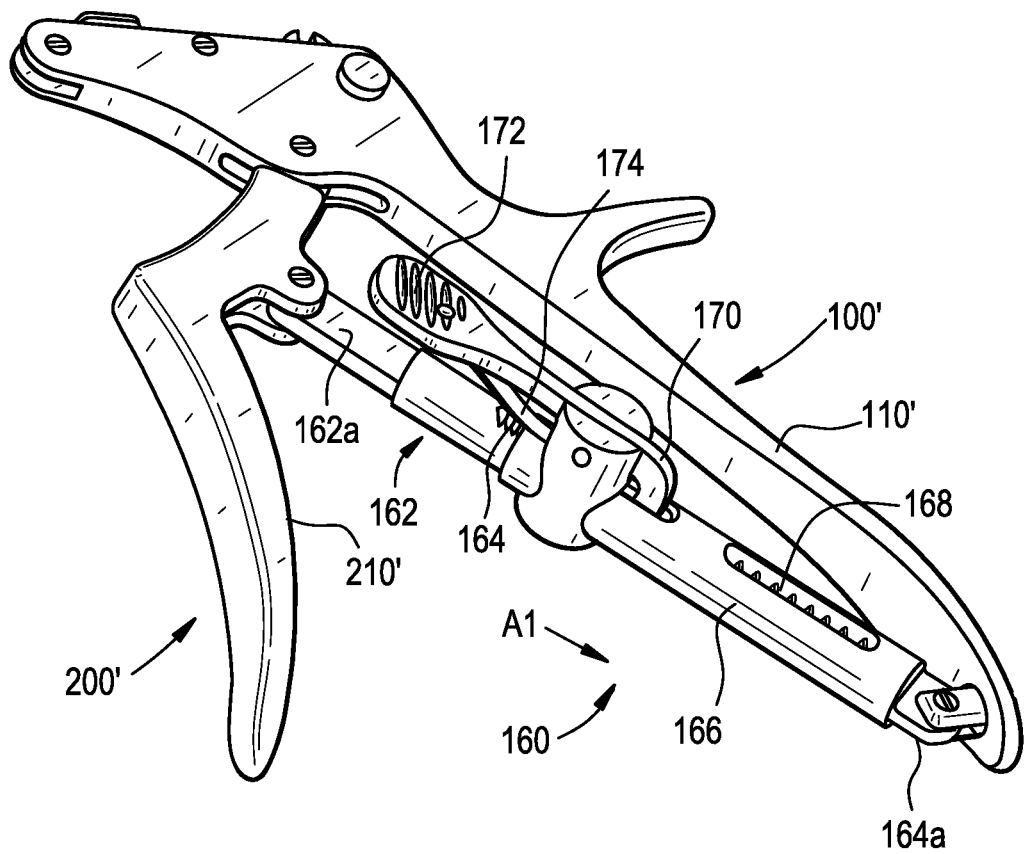
FIG. 4 is a perspective view of one exemplary embodiment of a lever locking/unlocking mechanism suitable for use with the embodiment rod reducer of FIG. 1A.

Alternatively, or additionally, in some embodiments, the disclosed rod reducer 10 can be configured to include a lever locking/unlocking mechanism to control the relative position of levers and thus control the rod-reduction range of motion. For example, a lever locking/unlocking mechanism can be useful to controllably override the self-returning nature of the levers, such that a rod can be "held" either partially or fully reduced, until released. For example, as shown in FIG. 4, in some embodiments, the lever locking/unlocking mechanism 160 can be configured to control the relative position of levers 100' and 200'.

Except as indicated below and as will be readily appreciated by one having ordinary skill in the art in view of the present disclosure, the structure and operation of the levers 100' and 200' is substantially the same as that of the levers 100 and 200 described above. Accordingly, a detailed description is omitted here for the sake of brevity. It will be appreciated that the levers 100' and 200' can include any of the features described herein with respect to the levers 100 and 200.

In the illustrated embodiment, the lever locking/unlocking mechanism 160 includes a piston 162 having ratchet teeth 164, a tubular housing 166 containing a compression spring 168, and a ratchet pawl 170 coupled to the tubular housing. The piston 162 can be slidably disposed within the tubular housing 164, such that the ratchet pawl 170 can engage the ratchet teeth 164. The piston 162 can be pivotally coupled to the body 210' of the second lever 200' at an end 162a. The tubular housing 164 can be pivotally coupled to the body 110' of the first lever 100' at an end 164a.

In operation, as the levers 100' and 200' are moved towards one another, the piston 162 slides further into the housing 166 (e.g., shown by arrow A1), thereby compressing the spring 168. When movement of the levers 100' and 200' towards one another stops (e.g., when the desired level of rod reduction is reached), the engagement of the ratchet pawl 170 and the ratchet teeth 164 locks the piston 162, and thus the relative position of the levers 100' and 200', in place. In some embodiments, the lever locking/unlocking mechanism 160 can also include a leaf spring 174 that applies an upward bias force against the ratchet pawl 170 to keep the ratchet pawl in engagement with the ratchet teeth 164. An advantage of the lever locking/unlocking mechanism 160 can include the ability to enable the rod reducer to maintain a desired rod reduction, either partial or full reduction, without the need to apply any additional external pressure to the levers 100' and 200'.

In some embodiments, the ratchet pawl 140 can include a release pad 172 for disengaging the pawl from the ratchet teeth 164 of the piston 162, and thereby unlock the levers 100' and 200' from a locked position. For example, by pressing downward on the release pad 172, the ratchet pawl 170 can tilt away and thus disengage from the ratchet teeth 164. When the ratchet pawl 170 releases from the ratchet teeth 164, the compressed spring 168 can expand and push against the piston 162. Thus, the piston 162 slides partially out of the tubular housing 166, such that the levers 100' and 200' can return to their original positions.

A person skilled in the art will recognize other design configurations are possible for the lever locking/unlocking mechanism 160, or aspects thereof (e.g., the piston 162 and housing 166), depending, at least in part, on the sizes, shapes, and configurations of other components of the rod reducer 10 and the intended use of the reducer, among other factors. Other possible design configurations for the locking/unlocking mechanism can include, but are not limited to, a lock-sleeve, a latch-bar, etc. For example, a lock-sleeve can have a configuration similar to the mechanism 160 shown in FIG. 4, without the ratcheting pawl and teeth. A latch-bar can have one end pivotally coupled to a first lever of the rod reducer and an opposing end configured as a ratcheting pawl to engage with counterpart ratcheting teeth disposed along an exterior surface of a second lever.

Figure 5A:
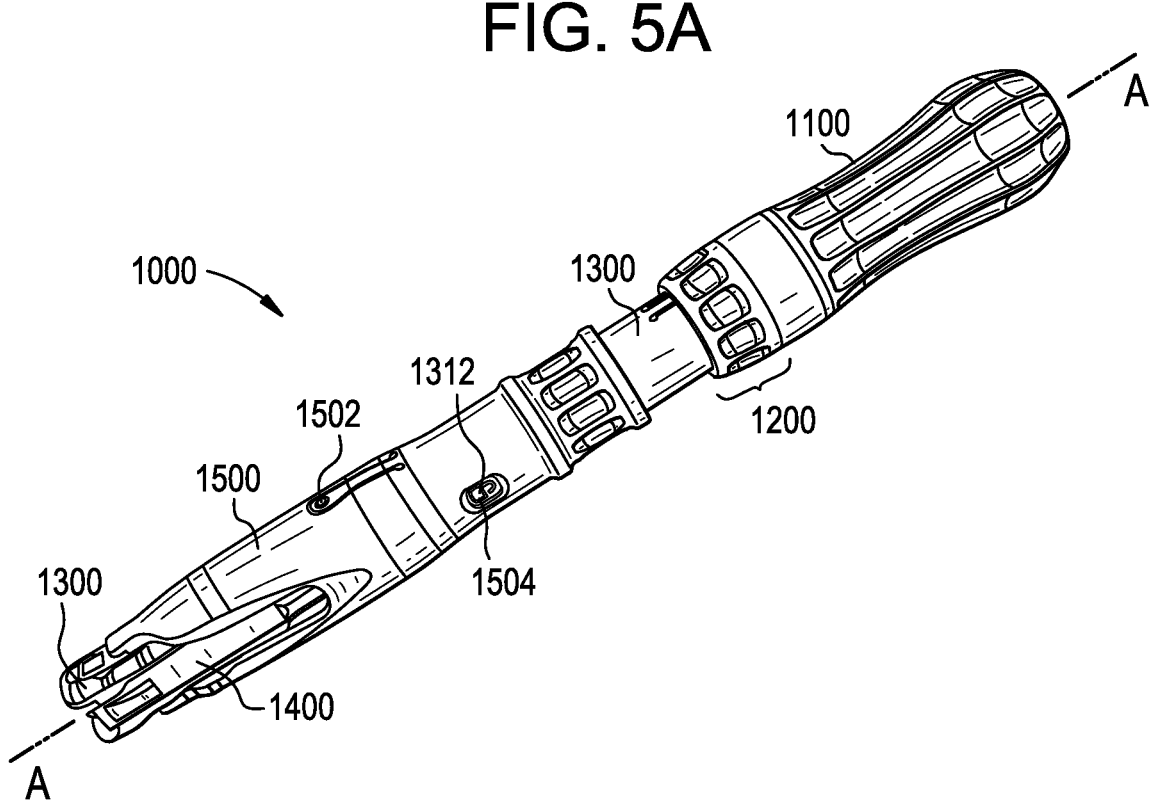
FIG. 5A is a perspective view of one exemplary embodiment of an inline rod reducer.
Figure 5B:
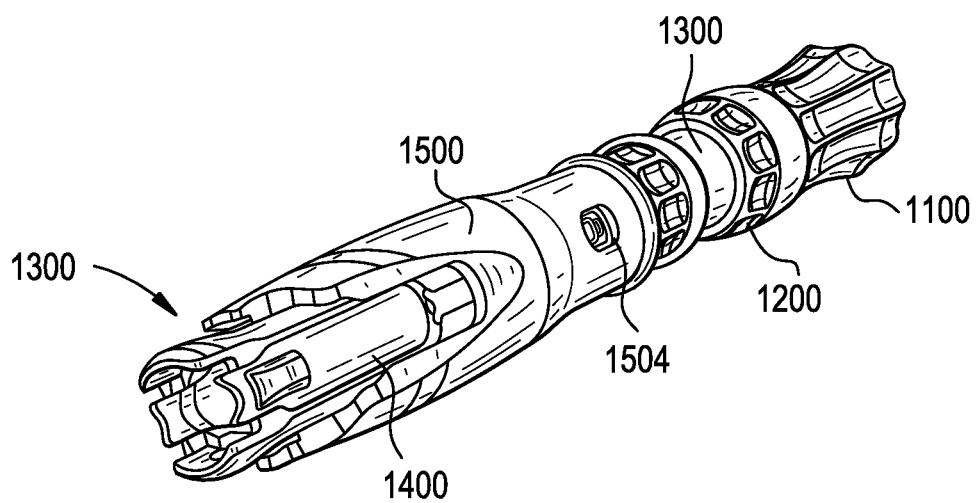
FIG. 5B is another perspective view of the rod reducer of FIG. 5A.

FIGS. 5A and 5B are schematic illustrations of another exemplary embodiment of a rod reducer. The rod reducer 1000 is an inline surgical instrument that includes multiple components coaxially aligned along a common longitudinal axis A-A. As shown in the illustrated embodiment, the rod reducer 1000 includes a handle 1100, a collar 1200, a gripping assembly 1300, a rod reducing component 1400, and a locking sleeve 1500. The gripping assembly 1300 can extend distally from the handle 1100 to receive and couple to a spinal implant. The rod reducing component 1400 can be disposed within a longitudinal passageway extending through, or at least partially through, the handle 1100 and the gripping assembly 1300. The rod reducing component 1400 can be moveably coupled to the handle 1100 such that the rod reducing component can be advanced or withdrawn through the passageway in response to a rotation of the handle. The locking sleeve 1500 can be slidably disposed around a portion of the gripping assembly 1300, such that one or more gripping elements lock onto the spinal implant when the locking sleeve 1500 is distally advanced over the gripping assembly 1300. The rod reducer 1000 can be disassembled into its constituent components 1100, 1200, 1300, 1400, and 1500 to facilitate cleaning and sterilization.

Figure 6A:
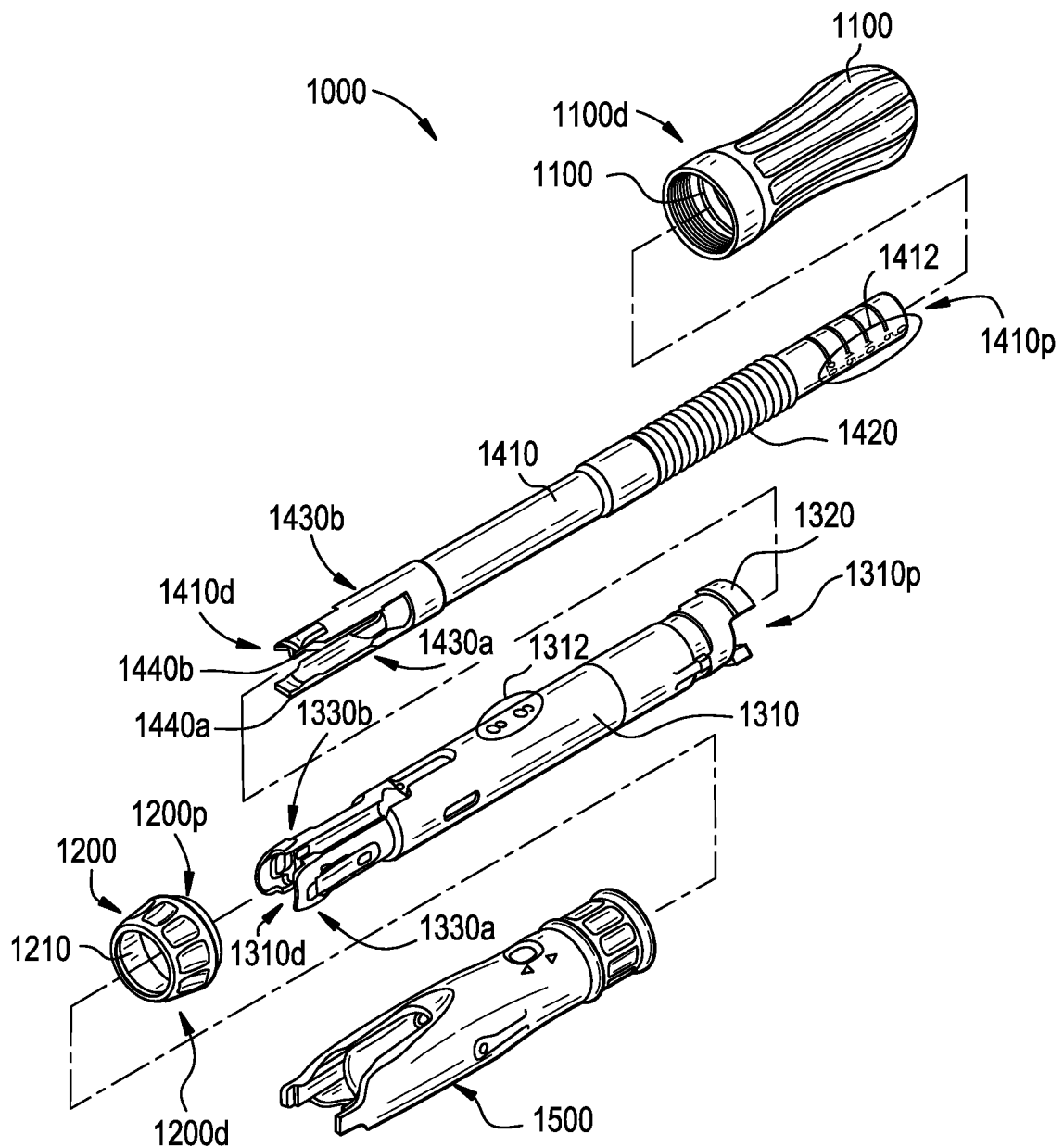
FIG. 6A is a perspective exploded view of components of the rod reducer of FIG. 5A.
Figure 6C:
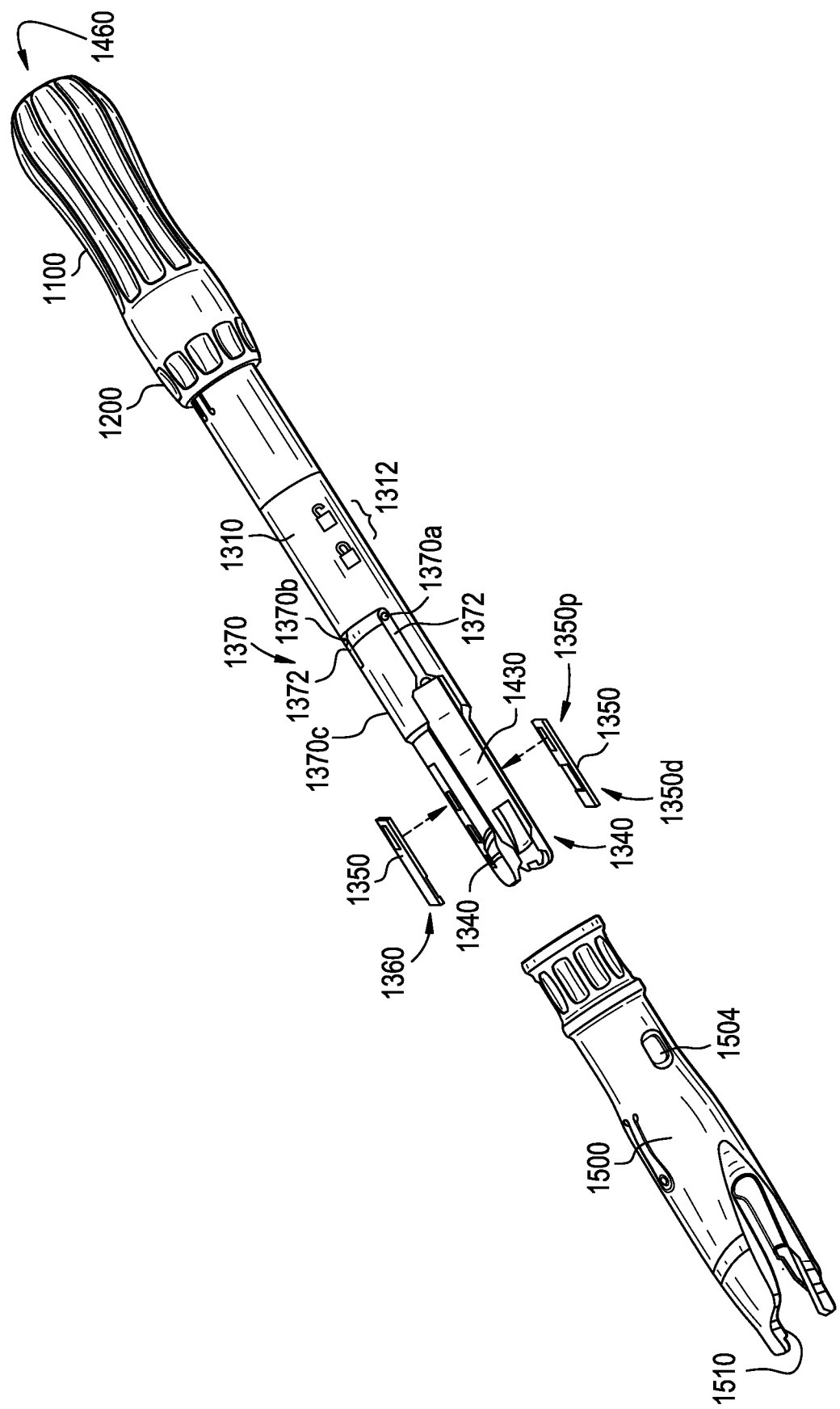
FIG. 6C is another perspective exploded view of components of the rod reducer of FIG. 5A.

As shown in more detail in FIGS. 6A-6C, the gripping assembly 1300 can include a substantially tubular shaft 1310 having a proximal end 1310p and a distal end 1310d. The proximal end 1310p of the tubular shaft 1310 can be loosely coupled to a distal end 1100d of the handle 1100 by a collar 1200. For example, the collar 1200 can have a proximal end 1200p fixedly coupled to the handle 1100 and a distal end 1200d defining an inner recess or pocket 1210 for loosely coupling to a ridge or other projection 1320 of the tubular shaft 1310. The loose coupling of the handle 1100 to the tubular shaft 1310 can prevent the gripping assembly 1300 from rotating in response to a rotation of the handle.

The distal end 1310d of the gripping assembly 1300 can have one or more distally-extending fingers 1330a and 1330b (collectively 1330) configured to receive, locate and align (sometimes referred to herein as "nest") an implant. For example, as shown, the fingers 1330 of the gripping assembly 1300 can be spaced apart to form a pocket that accommodates the size and shape of the implant. The inner surface of the fingers 1330 can define one or more structural features that are configured to nest one or more counterpart structural features of the implant. For example, in some embodiments, the one or more structural features defined in the fingers 1330 can include, without limitation, ridges, grooves, protrusions, and other contoured surfaces.

In some embodiments, the locking sleeve 1500 can be slidably disposed around a portion of the tubular shaft 1310 of the gripping assembly 1300 to cause one or more gripping elements of the assembly 1300 to lock onto or otherwise securely couple to an implant. For example, as shown in the illustrated embodiment of FIG. 6C, one or more of the distally-extending fingers 1330 of the gripping assembly 1300 can define a window 1340 configured to expose a portion of a received implant. Each window 1340 can be covered or at least partially covered by a cantilevered gripping element 1350 having an elongate flexible body. The proximal end 1350p of the cantilevered gripping element 1350 can be fixed to an outer surface of the finger adjacent to the window 1340. The distal end 1350d of the cantilevered gripping element 1350 can define a locking feature 1360 configured to engage a counterpart locking feature of the implant through the window. For example, in some embodiments, the locking feature 1360 of the cantilevered gripping element 1350 can include a ridge or other protrusion configured to mate with a notch, groove or other recess defined in the outer surface of the implant.

As the locking sleeve 1500 is advanced distally over a cantilevered gripping element 1350 (shown by arrows A in FIG. 6B), an inner wall 1510 of locking sleeve 1500 can press the distal end 1350d of the gripping element into the window 1340 to cause the locking feature 1360 to mate with a counterpart locking feature of the implant exposed through the window. Conversely, when the locking sleeve 1500 is withdrawn, the distal end 1350d of the cantilevered gripping element 1350 can retract from the window 1340 and thereby release the implant. In some embodiments, the cantilevered gripping element 1350 can be made of an elastic material so that the distal end 1350d of the gripping element 1350 can be pressed into the window 1340 when the locking sleeve 1500 is advanced over the fingers 1330 and retracted from the window 1340 when the locking sleeve is proximally withdrawn from the fingers. Thus, the locking sleeve 1500 can add strength to the gripping assembly 1300 such that the distal end of the gripping assembly can be prevented from splaying, flexing, or otherwise popping off the implant.

In some embodiments, a guide slot or groove 1370 can be defined in the outer surface of the tubular shaft 1310. The guide slot 1370 can be configured to slidably engage one or more detents 1502 that protrude from the inner wall 1510 of the locking sleeve 1500. The guide slot 1370 can be patterned to align the locking sleeve 1350 with the opposing fingers 1330. The guide slot 1370 can also be patterned to guide the distal and proximal movements of the locking sleeve with respect to the cantilevered gripping element(s) 1350 of the gripping assembly 1300, e.g., for respectively engaging and disengaging the implant through respective window(s) 1340 defined in the fingers 1330.

For example, in the illustrated embodiment, the guide slot 1370 can be patterned to couple the locking sleeve 1500 to the gripping assembly 1300 by sliding the sleeve proximally to a first position 1370a and then rotating the sleeve about the shaft 1310 to a second position 1370b in alignment with the fingers 1330 of the gripping assembly 1300. Once the locking sleeve 1500 is aligned with the fingers 1330 of the gripping assembly 1300, the sleeve can be moved distally to a third position 1370c such that the cantilevered gripping element(s) 1350 are pressed into engagement with an implant exposed through the window 1340. Conversely, the locking sleeve 1500 can be moved proximally from the third position 1370c back to the second position 1370b to withdraw the sleeve from the cantilevered gripping element(s) 1350. Indexing holes 1372 can be defined at the first, second and third positions within the guide slot 1370 that engage the detents 1502 of the locking sleeve 1500 to provide tactile and audible feedback to the operator while moving the locking sleeve along the slot.

In some embodiments, the locking sleeve 1500 can define a proximal indicator window 1504 that exposes one or more icons, text, colors, graphics or other indicators 1312 disposed on the outer surface of the tubular shaft 1310. The indicators 1312 can provide an indication of when the implant is locked onto or otherwise securely coupled to the gripping assembly 1300. For example, as shown in FIG. 6C, the indicators 1312 are locked and unlocked icons disposed on the outer surface of the tubular shaft 1310. The locked icon can be displayed through the indicator window 1504 when the locking sleeve is positioned such that the detent 1502 engages the third position 1370c in the guide slot 1370.

The rod reducing component 1400 can include a substantially tubular shaft 1410 having a proximal end 1410p and a distal end 1410d. The tubular shaft 1410 of the rod reducing component 1400 can be disposed within a longitudinal passageway that extends through, or at least partially through, the handle 1100 and the tubular shaft 1310 of the gripping assembly 1300. The tubular shaft 1410 can include a threaded portion 1420 that mates with a counterpart threaded portion 1110 of the handle 1100 such that the shaft 1410 can move in response to a rotation of the handle. In some embodiments, the distal end 1410d of the rod reducing component 1400 can include one or more distally-extending fingers 1430a and 1430b (collectively 1430). The fingers 1430 can define one or more recessed surfaces 1440a and 1440b (collectively 1440) configured to engage a rod. For example, the recessed surfaces 1440 can be shaped to contact and push a rod into a rod-receiving portion of an implant. In some embodiments, a pair of rod engaging recessed surfaces 1440 can be defined at the distal-facing edge of the rod reducing component 1400. The recessed surfaces 452 can be spaced apart to engage the rod within the perimeter of the rod-receiving portion of the implant.

As discussed above, the tubular shaft 1410 of the rod reducing component 1400 can include a threaded portion 1420 that mates with a counterpart threaded portion 1110 of the handle 1100 such that the shaft 1410 can move in response to a rotation of the handle. For example, when the handle 1100 is rotated in a first direction (e.g., clockwise), the shaft 1410 of the rod reducing component 1400 can be advanced through the passageway, thereby causing the rod-engaging recessed surfaces 1440 to engage and push a rod into a rod-receiving portion of a spinal implant held by the gripping assembly 1300. Conversely, when the handle 1100 is rotated in a second direction (e.g. counter-clockwise), the rod reducing component 1400 can be proximally withdrawn into the passageway, thereby causing the rod-engaging recessed surfaces 1440 to disengage from the rod.

In some embodiments, the rod reducing component 1400 can be configured to effect a rod reduction in a range between approximately 0 millimeters (mm) and approximately 40 mm. In some embodiments, the rod reduction can be greater than 40 mm. For example, the rod reducing component 1400 can be configured to effect a rod reduction of approximately 20 millimeters (mm). In some embodiments, the gripping assembly 1300, the rod reducing component 1400, and the locking sleeve 1500 can have respective lengths to achieve greater or lesser reduction capability. Depth marking 1412 can be printed or otherwise disposed along a portion towards the proximal end 1410p of the rod reducing shaft 1410. In some embodiments, the tubular shaft 1410 of the rod reducing component 1400 can define an open-ended passageway 1460 between the proximal and distal ends of the shaft. The passageway 1460 can have dimensions (e.g., diameter, width, cross-sectional profile, etc.) configured to allow insertion of a set screw, plug, or other closure mechanism to fix a rod seated in an implant held at the distal end of the gripping assembly 1300.

Advantages of the disclosed rod reducer 1000 can include the ability to lock or otherwise securely couple the implant to the reducer independently of the rod reduction. For example, as discussed above, the locking sleeve 1500 can be manipulated with respect to the gripping assembly 1300 in order to lock or other secure the implant to the distal end 1310*d* of the gripping assembly shaft 1310. In a separate step, the operator can then rotate the handle 1100 such that the rod reducing component 1400 moves distally to engage and push a rod partially or fully into a rod-receiving portion of the implant.

Alternatively or additionally, the disclosed rod reducer 1000 can be configured to provide greater amounts of rod reduction as compared to conventional rod reducers. In some embodiments, the extent of rod reduction can be increased by increasing the length of the rod reducing shaft 1410 and the threaded portion 1420 disposed along the shaft. For example, in the illustrated embodiment, the opened-ended passageway 1460, which extends through the handle 1100, can accommodate rod reducing shafts having any desired length.

Alternatively or additionally, the coaxial alignment of the constituent components 1100, 1200, 1300, 1400, 1500 of the disclosed rod reducer 1000 along a common longitudinal axis A-A can substantially reduce, if not eliminate, side loading forces experienced with some reduction instruments, such as those utilizing pistol grips, etc. For example, as discussed above in the illustrated embodiment, the implant can be locked or otherwise securely coupled to the gripping assembly 1300 by manipulating the locking sleeve 1500 axially and rotationally about the common longitudinal axis A-A. Further, by rotating the handle 1100 about the longitudinal axis A-A, the rod reducing component 1400 can move axially along the axis A-A to push a rod into a rod-receiving portion of the implant. Accordingly, the disclosed rod reducer 1000 can be operated in a manner that avoids an application of force and/or torque orthogonal or otherwise oblique from the axis A-A. The non-cantilever, coaxial alignment of the constituent components can also allow the reducer 1000 to be engaged and locked onto an implant, partially or fully reduced, and remain in place while one or more additional reducers 1000 are subsequently applied to additional implants, and thus providing the opportunity for sequential rod reduction, e.g., along a patient's spine without needing to disengage/reengage a reducer with multiple implants.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. As the described methods are merely exemplary embodiments, various other methods that include additional steps or include fewer steps are also within the scope of the present disclosure. As the described methods are merely exemplary embodiments, one skilled in the art will recognize that the devices, implants, and instruments described herein can be modified or adapted to adhere to approved instructions for surgical use and applicable surgical technique guides.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. Further, device sizes can also vary depending on the intended use and surgical site anatomy, and in some embodiments particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Although specific embodiments are described above, it should be understood that numerous changes may be made within the spirit and scope of the concepts described. Accordingly, the disclosure is not to be limited by what has been particularly shown and described. All publications and references cited herein are expressly incorporated herein by reference in their entirety.

The invention claimed is:
1. A surgical instrument, comprising:
a gripping assembly having a proximal end and a distal end, the distal end of the gripping assembly configured to hold a spinal implant;

a rod reducing assembly having a proximal end and a distal end, the distal end of the rod reducing assembly configured to engage a rod, a first lever pivotally coupled to the proximal end of the gripping assembly; and a second lever pivotally coupled to the first lever and the proximal end of the rod reducing assembly, wherein movement of the first lever and the second lever towards one another causes the first and second levers to pivot about the proximal end of the gripping assembly and causes the rod reducing assembly to translate distally relative to the gripping assembly, thereby pushing a rod distally into a rod-receiving portion of a spinal implant held by the gripping assembly, wherein the proximal end of the rod reducing assembly is pivotally coupled to the second lever by a pin that extends across a cavity defined at the proximal end of the rod reducing assembly, and wherein a portion of the second lever is received within the cavity defined at the proximal end of the rod reducing assembly.

2. The surgical instrument of claim 1, wherein the rod reducing assembly slides distally over the distal end of the gripping assembly.

3. The surgical instrument of claim 2, wherein the distal end of the gripping assembly comprises one or more cantilevered gripping elements configured to engage a portion of a spinal implant when the distal end of the rod reducing assembly slides distally over the distal end of the gripping assembly.

4. The surgical instrument of claim 1, wherein the rod reducing assembly translates distally with a pivoting motion that is offset by the first and second levers pivoting about the proximal end of the gripping assembly.

5. The surgical instrument of claim 1, wherein the pin has a cross-sectional profile configured to pivotally couple the proximal end of the rod reducing assembly to the second lever when the pin is rotated to a first position and to decouple the proximal end of the rod reducing assembly from the second lever when the pin is rotated to a second position.

6. The surgical instrument of claim 5, further comprising a lock/release mechanism comprising the pin fixedly coupled to a third lever disposed externally at the proximal end of the rod reducing assembly, wherein the pin is rotated into the second position when the third lever is manually rotated in a first rotational direction.

7. The surgical instrument of claim 6, wherein the lock/release mechanism further comprises a torsion spring configured to oppose rotation of the third lever in the first rotational direction and thereby bias the pin in the first position.

8. The surgical instrument of claim 1:
wherein the gripping assembly comprises a first elongate beam extending proximally from a distal inner tubular body configured to hold a spinal implant, and wherein the rod reducing assembly comprises a second elongate beam extending proximally from a distal outer tubular body, wherein the outer tubular body is slidably disposed around at least a portion of the inner tubular body of the gripping assembly and wherein the outer tubular body defines a distal-facing surface configured to engage a rod.

9. The surgical instrument of claim 8, wherein the inner tubular body of the gripping assembly comprises one or more gripping elements configured to engage the spinal implant in response to the outer tubular body of the rod reducing assembly translating distally over the inner tubular body.

10. The surgical instrument of claim 8:
wherein the inner tubular body of the gripping assembly is laterally offset from the first elongate beam of the gripping assembly, and wherein the outer tubular body of the rod reducing assembly is laterally offset from the second elongate beam of the rod reducing assembly.

11. The surgical instrument of claim 8, wherein the inner tubular body of the gripping assembly defines a longitudinal passageway through which a fastening mechanism is deployed to secure a rod seated in a rod-receiving portion of a spinal implant.

12. The surgical instrument of claim 1, wherein the second lever is received within an open-ended slot formed in the first lever.

13. A surgical instrument, comprising:
a gripping assembly having a first elongate beam extending proximally from a distal inner tubular body, the distal inner tubular body configured to hold a spinal implant;

a rod reducing assembly having a second elongate beam extending proximally from a distal outer tubular body that is slidably disposed around at least a portion of the inner tubular body of the gripping assembly such that the distal outer tubular body and the distal inner tubular body extend co-axially along a central longitudinal axis, the distal outer tubular body having a distal-facing surface configured to engage a rod;

a first lever pivotally coupled to a proximal end of the gripping assembly; and a second lever pivotally coupled to the first lever and a proximal end of the rod reducing assembly;

wherein movement of the first lever and the second lever towards one another causes the first and second levers to pivot about the proximal end of the gripping assembly and causes the rod reducing assembly to translate distally relative to the gripping assembly, thereby pushing a rod distally into a rod-receiving portion of a spinal implant held by the gripping assembly; and wherein a central longitudinal axis of the second elongate beam is disposed radially inward of a central longitudinal axis of the first elongate beam with respect to the central longitudinal axis of the distal outer tubular body and the distal inner tubular body.

14. A surgical instrument, comprising:
a gripping assembly having a first elongate beam extending proximally from a distal inner tubular body, the distal inner tubular body configured to hold a spinal implant;

a rod reducing assembly having a second elongate beam extending proximally from a distal outer tubular body, the distal outer tubular body having a distal-facing surface configured to engage a rod;

a first lever pivotally coupled to a proximal end of the gripping assembly; and a second lever pivotally coupled to the first lever and a proximal end of the rod reducing assembly;

wherein movement of the first lever and the second lever towards one another causes the first and second levers to pivot about the proximal end of the gripping assembly and causes the second elongate beam of the rod reducing assembly to translate distally along the first elongate beam of the gripping assembly, thereby pushing a rod distally into a rod-receiving portion of a spinal implant held by the gripping assembly;

wherein an outer surface of the second elongate beam contacts and translates distally along an outer surface of the first elongate beam.

15. The surgical instrument of claim 14, wherein the gripping assembly includes at least one guide pin protruding from the outer surface of the first elongate beam and the rod reducing assembly includes a longitudinal slot extending through the outer surface of the second elongate beam;

wherein the longitudinal slot of the second elongate beam slidably couples with the at least one guide pin of the first elongate beam.

16. The surgical instrument of claim 14, wherein the outer surface of the second elongate beam contacts the outer surface of the first elongate beam along substantially an entire length of the first elongate beam.

17. The surgical instrument of claim 14, wherein the outer surface of the second elongate beam contacts the outer surface of the first elongate beam at the proximal end of the gripping assembly.

* * * * *